(12) United States Patent
Chang et al.

(10) Patent No.: US 10,335,445 B2
(45) Date of Patent: Jul. 2, 2019

(54) COMPOSITIONS AND METHODS OF ANTIALLERGIC PHORBOL ESTER AND PHORBOL DERIVATIVES AS THE MAIN ACTIVE INGREDIENTS FROM THE SEEDS OF AQUILARIA MALACCENSIS

(71) Applicant: WE-WIN APPLIED BIO-TECH CO., LTD., Kaohsiung (TW)

(72) Inventors: Fang-Rong Chang, Kaohsiung (TW);
Bing-Hung Chen, Kaohsiung (TW);
Hsue-Yin Hsu, Kaohsiung (TW);
Yang-Chang Wu, Kaohsiung (TW);
Chen Hsieh, Kaohsiung (TW);
Hui-Ping Hsieh, Kaohsiung (TW)

(73) Assignee: WE-WIN APPLIED BIO-TECH CO., LTD., Kaohsiung (TW)

( * ) Notice: Subject to any disclaimer, the term of this patent is extended or adjusted under 35 U.S.C. 154(b) by 0 days.

(21) Appl. No.: 15/180,088

(22) Filed: Jun. 13, 2016

(65) Prior Publication Data
US 2017/0266250 A1    Sep. 21, 2017

(30) Foreign Application Priority Data
Mar. 16, 2016    (TW) .............................. 105108065 A

(51) Int. Cl.
| | | |
|---|---|---|
| *A61K 31/23* | (2006.01) |
| *A61K 36/835* | (2006.01) |
| *A61K 31/232* | (2006.01) |
| *A61K 31/231* | (2006.01) |
| *C07C 67/56* | (2006.01) |
| *C07C 67/58* | (2006.01) |
| *C07C 69/58* | (2006.01) |
| *C07C 69/587* | (2006.01) |
| *C07C 69/732* | (2006.01) |
| *C07C 69/738* | (2006.01) |

(52) U.S. Cl.
CPC ............ *A61K 36/835* (2013.01); *A61K 31/23* (2013.01); *A61K 31/231* (2013.01); *A61K 31/232* (2013.01); *C07C 67/56* (2013.01); *C07C 67/58* (2013.01); *C07C 69/58* (2013.01); *C07C 69/587* (2013.01); *C07C 69/732* (2013.01); *C07C 69/738* (2013.01); *A61K 2236/333* (2013.01); *A61K 2236/39* (2013.01); *C07C 2603/40* (2017.05)

(58) Field of Classification Search
CPC ..................................................... A61K 36/835
See application file for complete search history.

(56) References Cited

U.S. PATENT DOCUMENTS

2011/0160152 A1 *   6/2011   Wang ................... A61K 31/704
514/26

FOREIGN PATENT DOCUMENTS

WO    WO 2001082927    *  11/2001

* cited by examiner

*Primary Examiner* — Ana Z Muresan
(74) *Attorney, Agent, or Firm* — Leong C. Lei

(57) ABSTRACT

The present invention relates to phorbol esters from the seeds of *Aquilaria malaccensis* by a series of chromatographic processes, and compositions containing these congeners for the treatment of allergic responses.

5 Claims, 17 Drawing Sheets

| | Viability, RBL-2H3 | Inhibition of β-hexosaminidase release, degranulation assay, RBL-2H3 cells[a] | | | | Inhibitory effect on enzyme |
|---|---|---|---|---|---|---|
| | IC50 (μg/ml)[b] | A23187-induced | therapeutical index[c] | antigen-induced | therapeutical index[c] | β-hexosaminidase |
| sample | (% viability at 100 μg/ml) | IC50 (μg/ml)[b] | | IC50 (μg/ml)[b] | | (%)[d] |
| A-EtOH | >100 (86.0 %) | 0.92 | >109.0 | 3.9 | >25.7 | 12.7 ± 4.2 (100 μM) |
| A-BuOH | >100 (93.3 %) | 1.1 | >92.1 | 6.0 | >16.7 | 7.3 ± 5.5 (100 μM) |
| A-Water | >100 (94.0 %) | | | | | |
| A-EtOAc | >100 (90.3 %) | 0.56 | >177.9 | 0.86 | >116.8 | 13.3 ± 2.1 (100 μM) |
| A-Hexane | >100 (95.3 %) | 0.83 | >120.1 | 5.1 | >19.5 | 13.7 ± 2.5 (100 μM) |
| A-MeOH | 96.8 | 0.0089 | 10910.9 | 0.069 | 1405.2 | 5.3 ± 3.2 (100 μM) |
| AM4 | 98.0 | 0.0034 | 28677.6 | 0.0065 | 15098.4 | 4.7 ± 4 (100 μM) |
| AM4-4 | 70.6 | $4.8 \times 10^{-5}$ | 1477328.2 | $6.8 \times 10^{-4}$ | 103776.5 | |
| AM4-7 | 73.8 | $7.4 \times 10^{-4}$ | 99680.2 | 0.0065 | 11309.9 | |
| AM4-8 | 73.4 | $7.6 \times 10^{-6}$ | 9645374.3 | $8.0 \times 10^{-6}$ | 917440.9 | |
| AM4-9 | 71.5 | 0.0010 (0.0017 μM) | 71538.5 | 0.0068(0.011 μM) | 10550.2 | 4.3 ± 4.5 (100 μM) |

[a] dexamethasone (10 nM) inhibited 54.0 ± 4.0 % of A23187-induced β-hexosaminidase release and 54.3 ± 7.2 % of antigen-induced β-hexosaminidase release

[b] IC50 values express the concentration of the sample required to inhibit cell growth or degranulation by 50%

[c] therapeutic index was calculated by dividing IC50 value from MTT viability assay with corresponding IC50 value from degranulation assay

[d] results are presented as mean ± SD (n = 3)

Fig. 16

| sample | Superoxide anion generation (Inh %) | | Elastase release (Inh %) | |
|---|---|---|---|---|
| A-EtOH | 90.1 ± 5.3 | ** | 85.3 ± 0.8 | ** |
| A-BuOH | 93.9 ± 8.3 | ** | 77.6 ± 2.4 | ** |
| A-Water | 11.4 ± 8.3 | * | 2.7 ± 4.1 | |
| A-EtOAc | 94.8 ± 5.6 | ** | 85.4 ± 1.8 | ** |
| A-Hexane | 10.3.4 ± 1.8 | ** | 80.2 ± 4 | ** |
| A-MeOH | 96.5 ± 8.0 | ** | 90.4 ± 6.0 | ** |
| AM1 | 54.5 ± 5.7 | ** | 99.2 ± 2.3 | ** |
| AM2 | 68.7 ± 5.0 | ** | 47.5 ± 5.3 | ** |
| AM3 | 105.9 ± 3.4 | ** | 86.8 ± 2.0 | ** |
| AM4 | 100.7 ± 8.1 | ** | 70.9 ± 1.0 | ** |
| AM5 | 102.6 ± 1.5 | ** | 93.5 ± 3.7 | ** |
| AM6 | 102.4 ± 2.0 | ** | 99.3 ± 2.3 | ** |

Fig. 17

| sample | HepG2 | MDA-MB231 | A549 |
|---|---|---|---|
| A-EtOH | 16.0 | 37.2 | 29.7 |
| A-BuOH | 4.2 | 34.4 | 57.1 |
| A-Water | -9.3 | 6.8 | 13.3 |
| A-EtOAc | 1.5 | 41.2 | 23.5 |
| A-Hexane | 25.1 | 42.5 | 16.8 |
| A-MeOH | -0.8 | 30.3 | 32.7 |
| AM1 | 8.1 | 1.7 | -12.6 |
| AM2 | 2.4 | 11.5 | 19.8 |
| AM3 | 25.5 | 46.3 | 39.5 |
| AM4 | 23.4 | 56.5 | 79.3 |
| AM5 | 7.9 | 39.9 | 29.2 |
| AM6 | 5.3 | 56.0 | 39.5 |
| doxorubicin | 91.3 | 97.9 | 98.0 |

Fig. 18

ND METHODS OF
ANTIALLERGIC PHORBOL ESTER AND
PHORBOL DERIVATIVES AS THE MAIN
ACTIVE INGREDIENTS FROM THE SEEDS
OF AQUILARIA MALACCENSIS (a) TECHNICAL FIELD OF THE INVENTION

Compositions and methods of antiallergic phorbol ester and phorbol derivatives as the main active ingredients from the seeds of *Aquilaria malaccensis*.

(b) DESCRIPTION OF THE PRIOR ART

It is known that allergic diseases are the hypersensitive immuno-response induced by specific foods or a number of factors in the environment that usually arouse some indispositions, such as allergic rhinitis, urticaria, atopic dermatitis, asthma, and even severe anaphylaxis. The symptoms involve red eyes, itchy rashes, rhinorrhea, dyspnea, and swelling. Therefore, some foods and the factors in the environment are so-called allergens. However, the environment is getting polluting by the growth of industry development, and the green lands and forests such as the Brazilian rainforest are substantively lost by the land development. The phenomenon in number increase and age decline of patients with allergic diseases is observed and arisen from the changed climate and environment due to above reasons.

IgE-mediated allergy is a common immune system disorder, and the combinations with allergens release inflammatory chemicals such as histamine. Current treatments for allergies include the avoidances of known allergens and the usages of corticosteroids and antihistamines; additionally, the intravenous injection of epinephrine would be applied for suppressions of hypersensitive responses when severe allergies occurred. Importantly, mast cells and their degranulation play a crucial role in IgE-mediated allergic inflammatory responses such as allergic rhinitis, acute asthma, and atopic eczema (Lian et al., Int. J. Mol. Sci., 16, 2252-2268, 2015). Beta-hexosaminidase is an enzyme released along with histamine from mast cells (RBL-2H3 cells) upon activation and serves as a well-accepted in vitro model in allergy (Dearman et al., Toxicology, 206, 195-205, 2005). Although today we are able to treat the symptoms of allergy, available medications have undesirable effects, especially within a prolonged use. Therefore, there is a need to search for alternative treatment, and natural sources are often considered as safe and easily available.

Agarwood is a priceless fragrant resinous wood from *Aquilaria* species (Thymelaeaceae), which is formed as a defense mechanism to fend off pathogens. Agarwood is widely applied in traditional medicine preparations for cardiotonic, carminative, antiasthmatic, aphrodisiac, astringent remedy. Moreover, *Aquillaria* agarwood has been found effective against diarrhea, dysentery, gout, rheumatism, paralysis and parasites, and it has been beneficial for skin diseases (Talukdar et al, Int. J. Pharm. Pharm. Sci., 6, 629-631, 2014). Furthermore, *Aquilaria* species was previously found to possess antidepressant (Yang et al., J. Nat. Prod., 76, 216-222, 2013; Huong et al., Nat. Prod. Sci., 8, 30-33, 2002), anti-neuroinflammatory (Huo et al., Fitoterapia, 106, 115-121, 2015), analgesic, antiinflammatory (Zhou et al., J. Ethnopharmacol., 117, 345-350, 2008), antioxidant, antibacterial (Kamonwannasit et al., Ann. Clin. Microbiol. Antimicrob., 12, 20, 2013) in vitro assays whereas antihyperglycemic and laxative activity in vivo (Pranakhon et al., Pharmacogn. Mag., 11, 82-89, 2015; Hara et al., Biosci. Biotechnol. Biochem., 72, 335-345, 2008).

In particular, the alcoholic extract of *A. malaccensis* stein and bark exhibited cardiotonic activity (Pant et al., Phytochemistry, 19, 1869-1870, 1980), and cytotoxicity against Eagle's carcinoma of the nasopharynx and P-388 lymphocytic leukemia cells in vitro (Gunasekera et al., J. Nat. Prod., 44, 569-572, 1981). The aqueous extract showed antitrypanosomal (Dyary et al., Trop. Biomed., 31, 89-96, 2014), antibacterial (Dash et al., Afr. J. Biotechnol., 7, 3531-3534, 2008), and antiallergic activity in vitro and in vivo (Kiln et al., J. Ethnopharmacol., 58, 31-38, 1997). In the previous phytochemical investigation of *A. malaccensis* stein bark, an anticancer phorbol ester, 12-O-(2Z,4E,6E)-deca-2,4,6-trienoylphorbol-13-acetate was isolated (Gunasekera et al., J. Nat. Prod., 44, 569-572, 1981). The phorbol ester belongs to the tigliane esters, a class of compounds are well recognized as being irritant, proinflammatory and cocarcinogenic. However, no any further studies of this phytochemical on anti-allergy was conducted, and therefore its antiallergic properties still unknown.

On the other hand, it is too slow growth of *Aquilaria malaccensis* to supply the stein and bark extracts plentifully and permanently. Relative to the stems and barks of agarwood (*A. malaccensis*), the seeds of *A. malaccensis* were easier to be obtained and thus chosen for alternative investigation to prevent and treat allergic diseases. In the present invention, the preparation methods, the compositions, and the bioactive assays including antiallergic, antiinflammatory, and cytotoxic tests of *A. malaccensis* seeds (AMS) extract, its fractions, and those isolated phorbol esters with formulas I~IV were designed and achieved.

SUMMARY OF THE INVENTION

The primary object of the present invention is to provide antiallergic compositions from the seeds of *Aquilaria malaccensis* and their preparation methods.

The second object of the present invention is to provide compositions from the seeds of *Aquilaria malaccensis* to prevent and treat the allergies and related hypersensitive immuno-responses effectively.

These objects will become apparent as description of the invention proceeds. In accordance with this invention, the methods of preparation are following:
(a) Air-dried and powdered seeds of *A. malaccensis* (462 g) were extracted with 90% ethanol at room temperature (3×5 L) and then concentrated under reduced pressure.
(b) The combined extracts were concentrated and an obtained ethanolic extract (EtOH, 27.7 g) was suspended in water and partitioned with ethyl acetate (EtOAc, 3×1 L).
(c) The organic (EtOAc) layer (25.6 g) was further partitioned with n-hexane and 90% aqueous methanol (MeOH) to obtain a low-polar (Hexane) layer (7.1 g) and a high-polar (MeOH) layer (16.2 g).
(d) The MeOH layer was subjected to a column chromatography over silica gel (23 cm×4 cm, silica gel 60, 0.063-0.200 mm, Merck) under a gradient elution of n-hexane/$CH_2Cl_2$/MeOH to yield six fractions (AM1, 6:3:1; AM2, 6:4:1; AM3, 6:6:1; AM4, 6:8:1; AM5, 6:10:1 and AM6, 6:10:2).
(e) Following bioactivity data, fraction AM4 (3212.0 g) was further fractionated over a Sephadex LH-20 column ($CH_2Cl_2$/MeOH, 1:1) to obtain eight sub-fractions (AM4-1 to AM4-8).
(f) Fraction AM4-3 (762.0 mg) was subjected to column chromatography (17 cm×4 cm, Geduran Si 60, 0.040~0.063 mm, Merck) under gradient elution of EtOAc/n-hexane (from 1:10 to 4:1) yielding 15 fractions AM4-3-1~AM4-3-15.
(g) Fraction AM4-4 (173.7 mg) was further separated by column chromatography on silica gel (30 cm×1.5 cm, Geduran Si 60, 0.040~0.063 mm, Merck) under gradient elution of EtOAc/n-hexane (from 1:15 to 4:1) to obtain 12 subfractions AM4-4-1~AM4-4-12.

In accordance with the preparation methods, a new phorbol ester of Formula I was isolated from AM4-4-9.

Formula I

In accordance with the preparation methods, a new phorbol ester of Formula II reported by now was isolated from AM4-3-6 and AM4-4-3.

Formula II

In accordance with the preparation methods, a new phorbol ester of Formula III reported by now was isolated from AM4-3-13.

Formula III

In accordance with the preparation methods, a new phorbol ester of Formula IV reported by now was also isolated from AM4-3-13.

Formula IV

In accordance with the preparation methods, two known phorbol esters of Formulas V and VI were isolated from AM4-4-7 and AM4-4-8, respectively.

Formula V

Formula VI

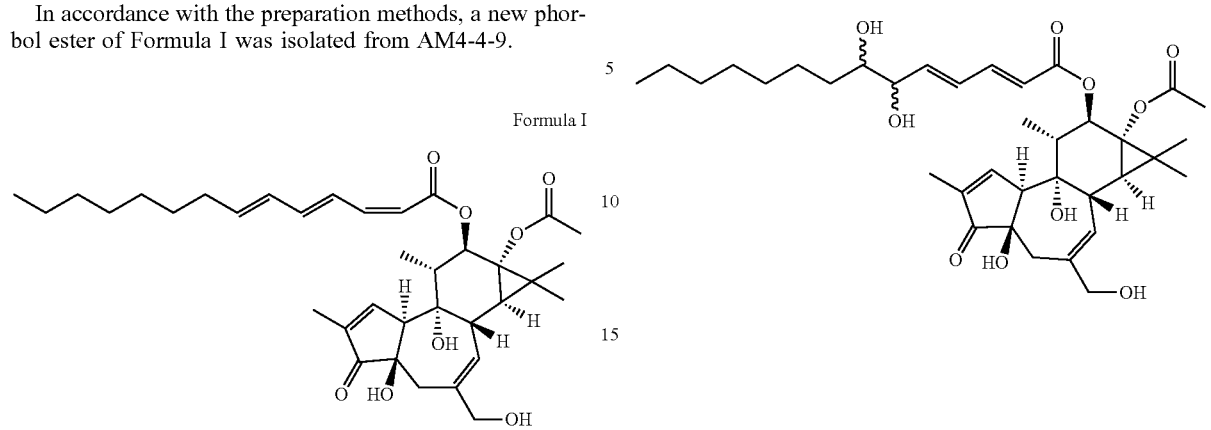

The third object of the present invention is to provide compositions from the seeds of *Aquilaria malaccensis* to prevent and treat the allergies and related hypersensitive immuno-responses effectively, of which compositions comprise a compound represented by Formula I to VI and their isomers or a or a pharmaceutically acceptable salt thereof as an active ingredient.

BRIEF DESCRIPTION OF THE DRAWINGS

FIG. 16. shows antiallergic activities of the compositions from *Aquilaria malaccensis* seeds by inhibition of β-hexosaminidase release.

FIG. 17. shows Antiinflammatory effects of the compositions from *Aquilaria malaccensis* seeds on superoxide anion generation and elastase release in fMLP/CB-induced human neutrophils.

FIG. 18. shows Cytotoxic activities of the compositions from *Aquilaria malaccensis* seeds against HepG2, MDA-MB231, and A549 carcinoma cell lines.

DETAILED DESCRIPTION OF THE PREFERRED EMBODIMENTS

The present invention is further illustrated by the preparation schemes (FIG. 1~3), the NMR spectra of phorbol esters represented by Formulas I to VI (FIG. 4~15), and the bioactive results (Tab. 1~4), and the skills and methods used herein are described in detail:
(a) After air-dried and powdered, the seeds of *A. malaccensis* (462 g) were extracted with 90% EtOH (5 L) at room temperature in triplicate and then concentrated under reduced pressure to afford an ethanolic extract (27.7 g).

Figure 1:
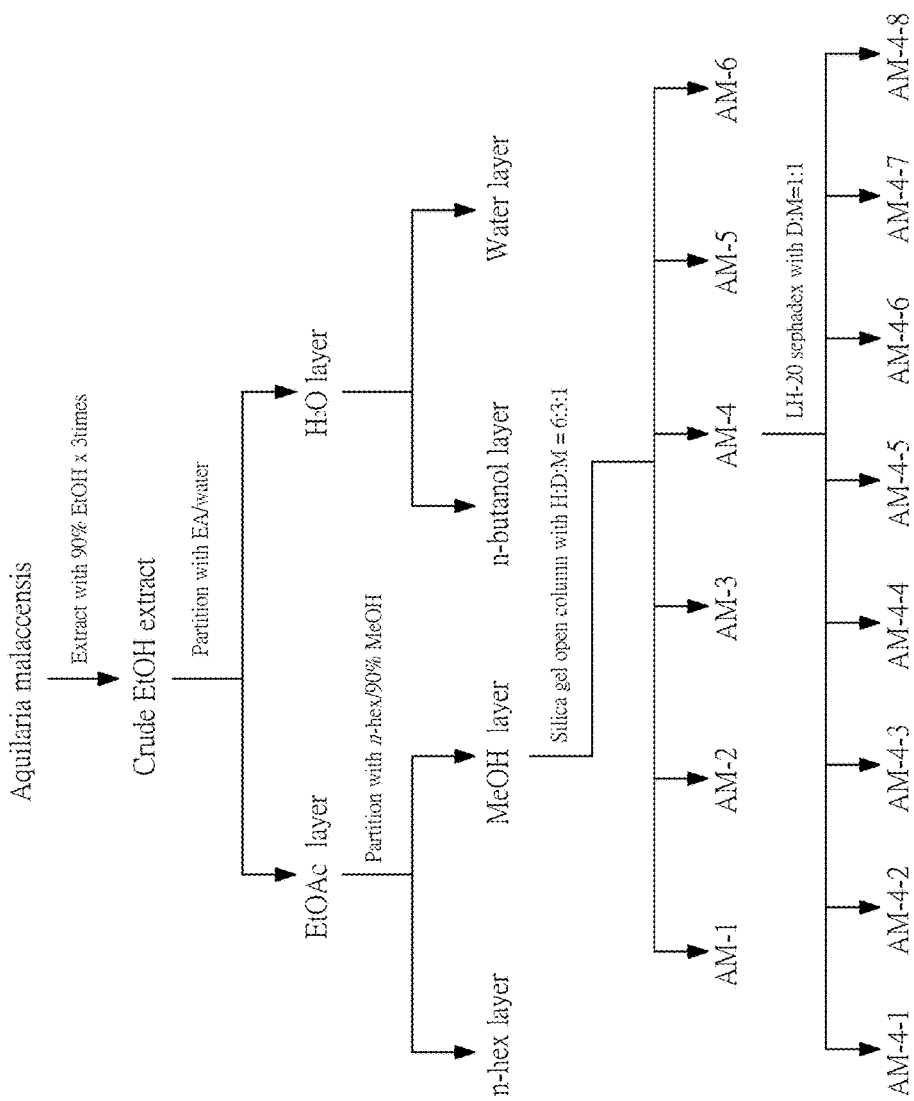
FIG. 1. shows preparation scheme of the present invention.
Figure 2:
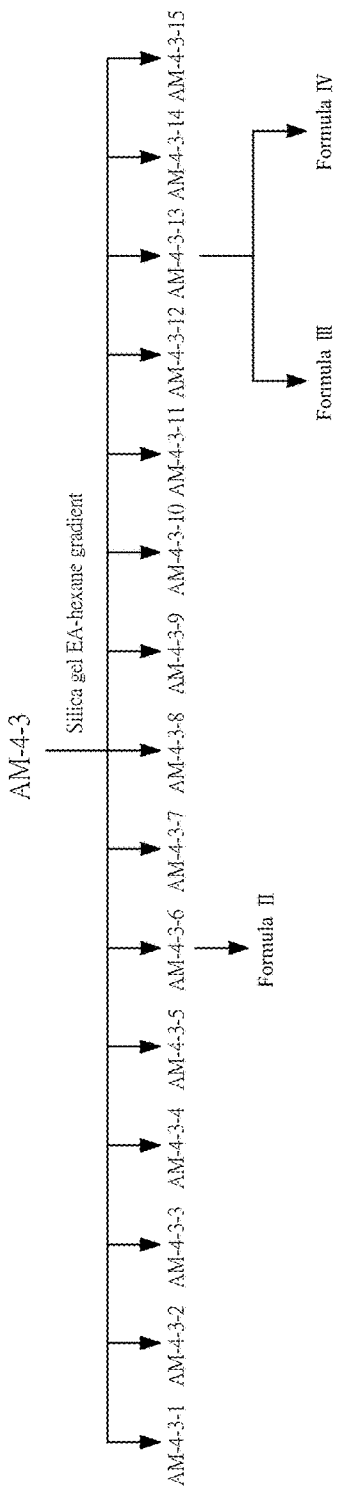
FIG. 2. shows isolation scheme of AM4-3 to afford 15 subfractions.
Figure 3:
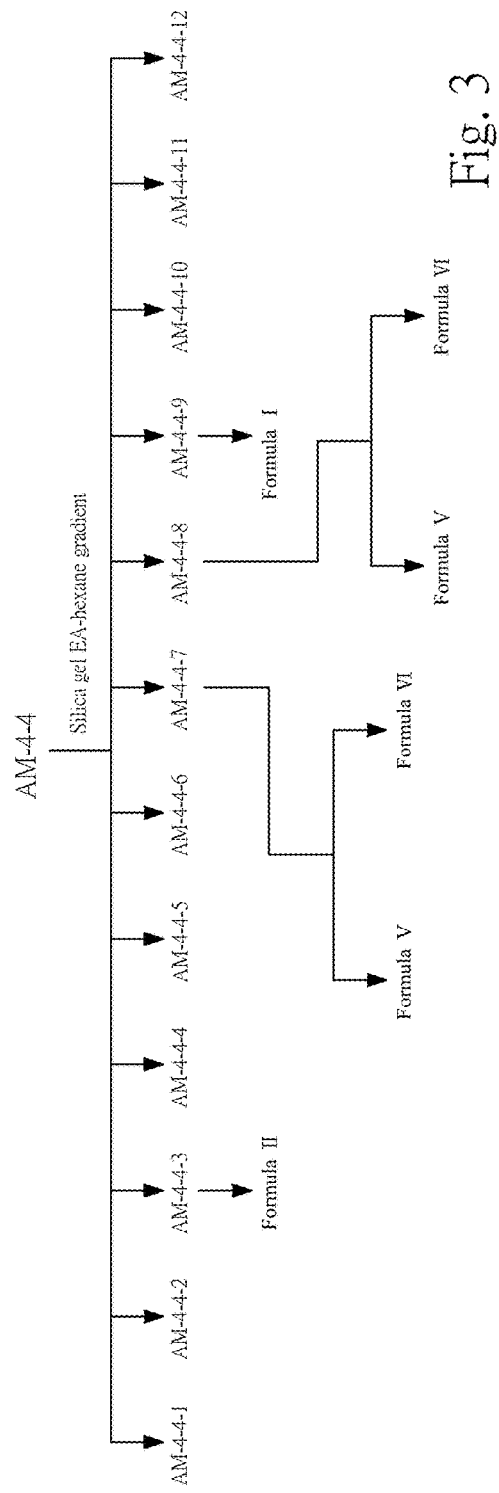
FIG. 3. shows isolation scheme of AM4-4 to afford 12 subfractions.
Figure 4:
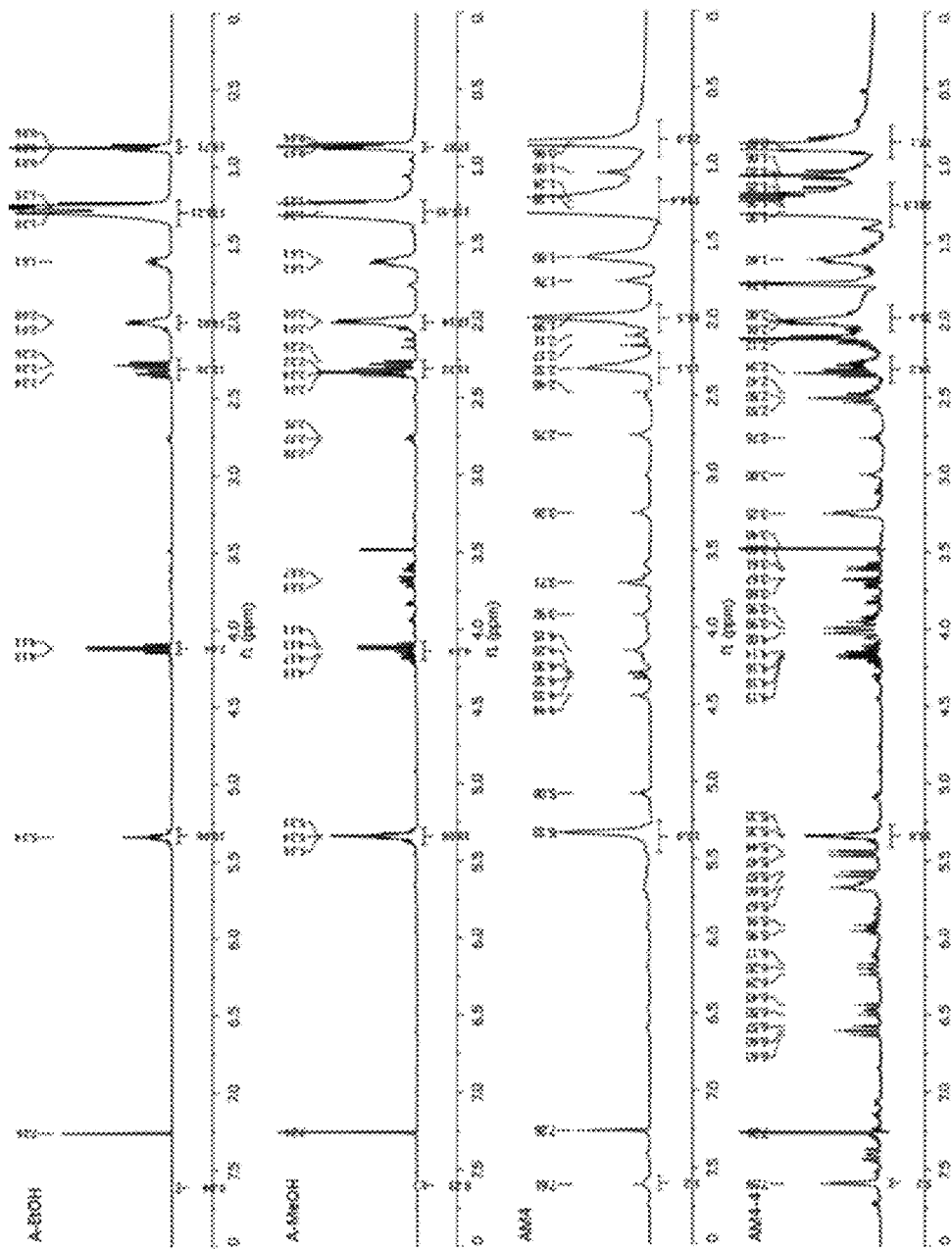
FIG. 4. shows $^1$H NMR spectra comparison of selected compositions from *Aquilaria malaccensis* seeds, the ethanolic extract (EtOH), 90% aqueous methanol layer (MeOH), AM-4, and AM4-4.

(b) The ethanolic extract was suspended in water (1 L) and partitioned with equivalent ethyl acetate in triplicate, an organic (EtOAc) layer (25.6 g) and an aqueous (H$_2$O) layer were separated.
(c) The EtOAc layer was further partitioned with n-hexane and 90% aqueous MeOH to obtain n-hexane layer (7.1 g) and MeOH layer (16.2 g) whereas the H$_2$O layer was further partitioned with n-butanol to divide into an n-butanol (BuOH) layer and an aqueous (Water) layer.
(d) The MeOH layer was subjected to a column chromatography over silica gel (23 cm×4 cm, silica gel 60, 0.063~0.200 mm, Merck) under a gradient elution of n-hexane/CH$_2$Cl$_2$/MeOH (6:3:1, 6:4:1, 6:6:1, 6:8:1, 6:10:1, and 6:10:2) to yield six fractions (AM1, 2917.0 mg; AM2, 1320.0 mg; AM3, 6834.0 mg; AM4, 3212.2 mg; AM5, 1703.0 mg; and AM6, 97.9 mg).
(e) Fractions AM4 was further fractionated over a Sephadex LH-20 column (CH$_2$Cl$_2$/MeOH, 1:1) to obtain eight subfractions (AM4-1, 688.0 mg; AM4-2, 688.0 mg; AM4-3, 762.0 mg; AM4-4, 173.7 mg; AM4-5, 609.0 mg; AM4-6, 253.5 mg; AM4-7, 80.0 mg; and AM4-8, 80.0 mg). Of which subfractions, AM4-3 and AM4-4 are phorbol ester-rich fractions. The above scheme are shown in FIG. 1.
(f) Fraction AM4-3 was subjected to column chromatography (17 cm×4 cm, Geduran Si 60, 0.040~0.063 mm, Merck) under gradient elution of EtOAc/n-hexane (from 1:10 to 4:1) yielding 15 fractions AM4-3-1~AM4-3-15 (FIG. 2). (AM4-3-1, 3.4 mg; AM4-3-2, 25.3 mg; AM4-3-3, 345.6 mg; AM4-3-4, 49.2 mg; AM4-3-5, 16.4 mg; AM4-3-6, 39.5 mg; AM4-3-7, 8.4 mg; AM4-3-8, 3.8 mg; AM4-3-9, 42.7 mg; AM4-3-10, 23.0 mg; AM4-3-11, 42.5 mg; AM4-3-12, 43.5 mg; AM4-3-13, 23.5 mg; AM4-3-14, 7.9 mg; and AM4-3-15, 38.3 mg) Of which subfractions, AM4-3-6 and AM4-3-13 are two phorbol ester-rich fractions.
(g) Fraction AM4-4 was further separated by column chromatography on silica gel (30 cm×1.5 cm, Geduran Si 60, 0.040~0.063 mm, Merck) under gradient elution of EtOAc/n-hexane (from 1:15 to 4:1), and 12 subfractions AM4-4-1~AM4-4-12 were obtained (FIG. 3). (AM4-4-1, 2.2 mg; AM4-4-2, 16.3 mg; AM4-4-3, 3.5 mg; AM4-4-4, 5.7 mg; AM4-4-5, 7.7 mg; AM4-4-6, 11.5 mg; AM4-4-7, 37.6 mg; AM4-4-8, 6.8 mg; AM4-4-9, 43.9 mg; AM4-4-10, 3.3 mg; AM4-4-11, 3.5 mg; and AM4-4-12, 23.5 mg) Of which subfractions, AM4-4-3, AM4-4-7, AM4-4-8 and AM4-4-9 are four phorbol ester-rich fractions.
(h) From AM4-4-9, a new phorbol ester named 12-O-(2Z,4E,6E)-tetradeca-2,4,6-trienoylphorbol-13-acetate (43.9 mg) was isolated. This compound possesses a molecule of C$_{36}$H$_{50}$O$_8$ and is represented by Formula I:

Formula I

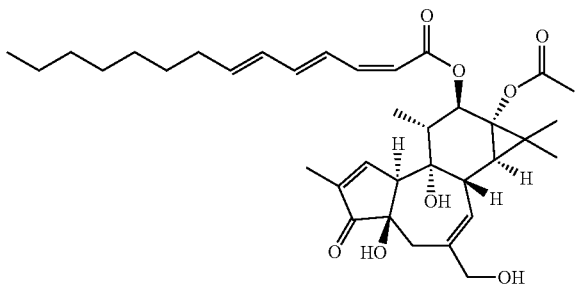

(i) From AM4-3-6 and AM4-4-3, a new phorbol ester named 12-deoxy-13-O-acetoylphorbol-20-octadec-9-enoate (8.8 mg) was afforded. This compound possesses a molecule of C$_{40}$H$_{62}$O$_7$ and is represented by Formula II:

Formula II

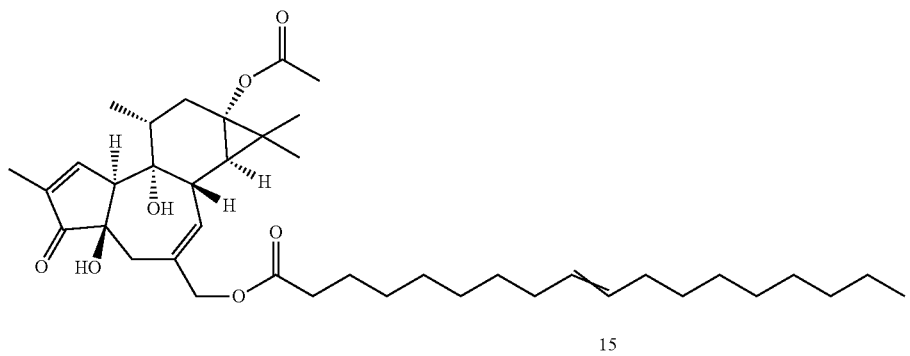

(j) From AM4-3-13, two new phorbol esters were given. One new phorbol ester named 12-O-(2E,4E)-6-oxohexa-2,4-dienoylphorbol-13-acetate (0.7 mg) with a molecule of $C_{28}H_{34}O_9$ is represented by Formula III. Another new phorbol ester named 12-O-(2E,4E)-6,7-dihydroxytetradeca-2,4-dienoylphorbol-13-acetate (0.9 mg) possesses a molecule of $C_{36}H_{52}O_{10}$ and is represented by Formula IV.

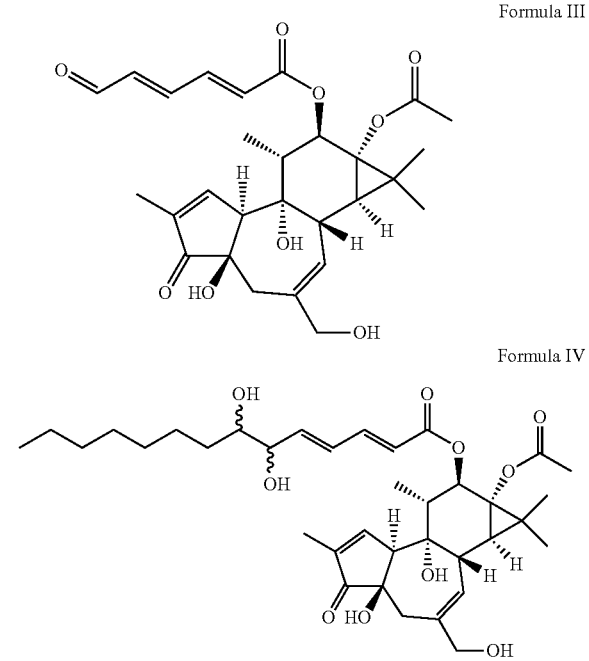

Formula III

Formula IV (k) From AM4-4-7 and AM4-4-8, two known phorbol esters, 12-deoxyphorbol 13-decanoate (8.5 mg) and 12-deoxyphorbol 13-octanoate (1.4 mg), were isolated. These two compounds possess molecules H of $C_{30}H_{46}O_6$ and $C_{28}H_{42}O_6$ and are represented by Formulas V and VI, respectively.

Formula V

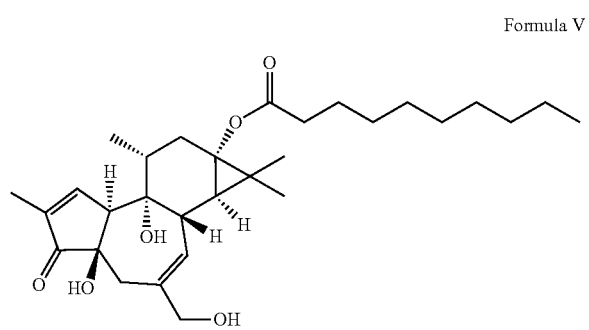

-continued

Formula VI

Analysis of the $^1H$ NMR spectra comparison of the ethanolic extract (EtOH), 90% aqueous methanol layer (MeOH), AM-4, and AM4-4 (FIG. 4), the EtOH extract, MeOH layer, AM-4, and the subfraction AM4-4 all comprise phorbol esters, and the efficacy of anti-allergy is in proportion to the signal strength of phorbol esters.

Figure 5:
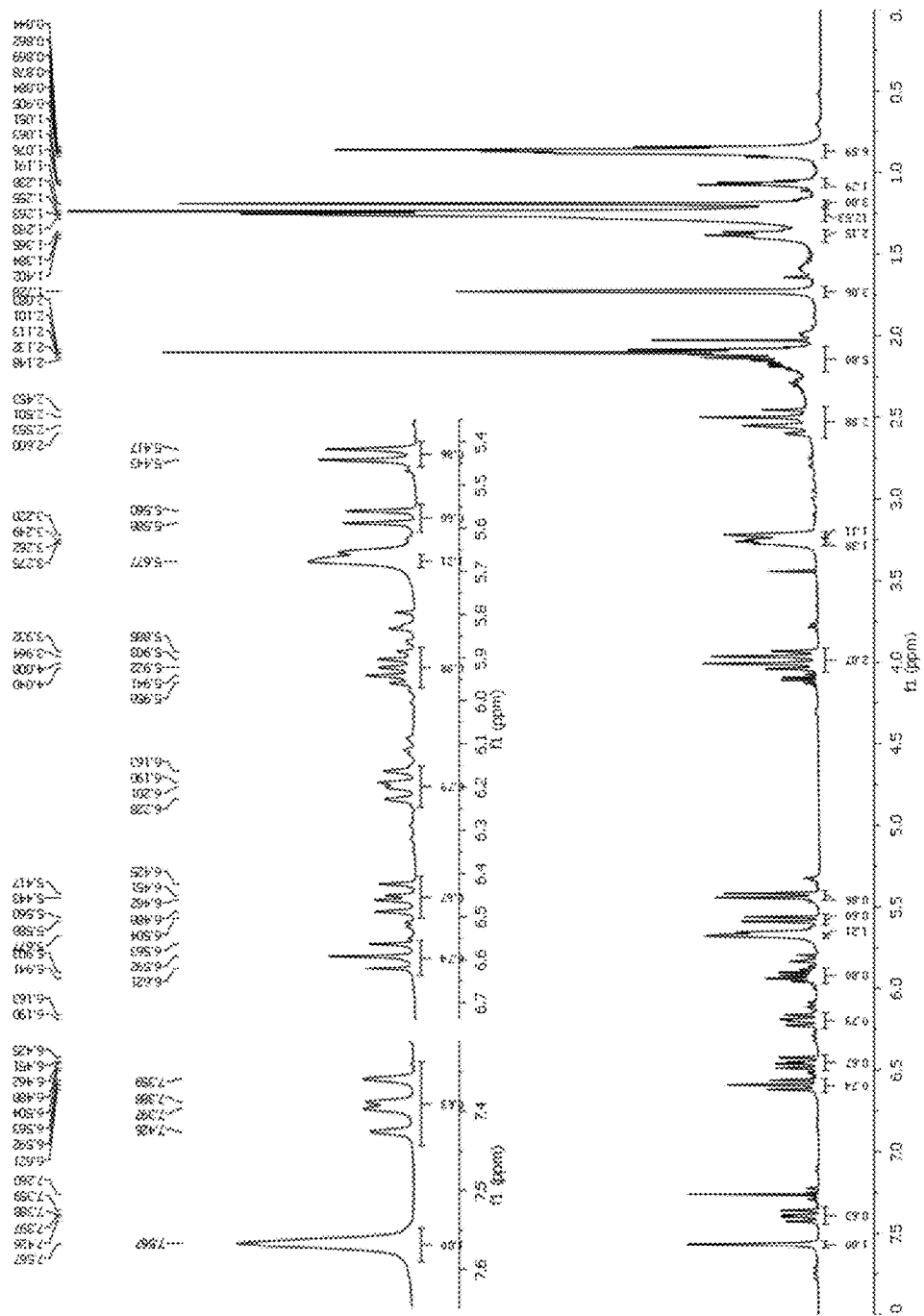
FIG. 5. shows $^1$H NMR spectrum of compound represented by Formula I.
Figure 6:
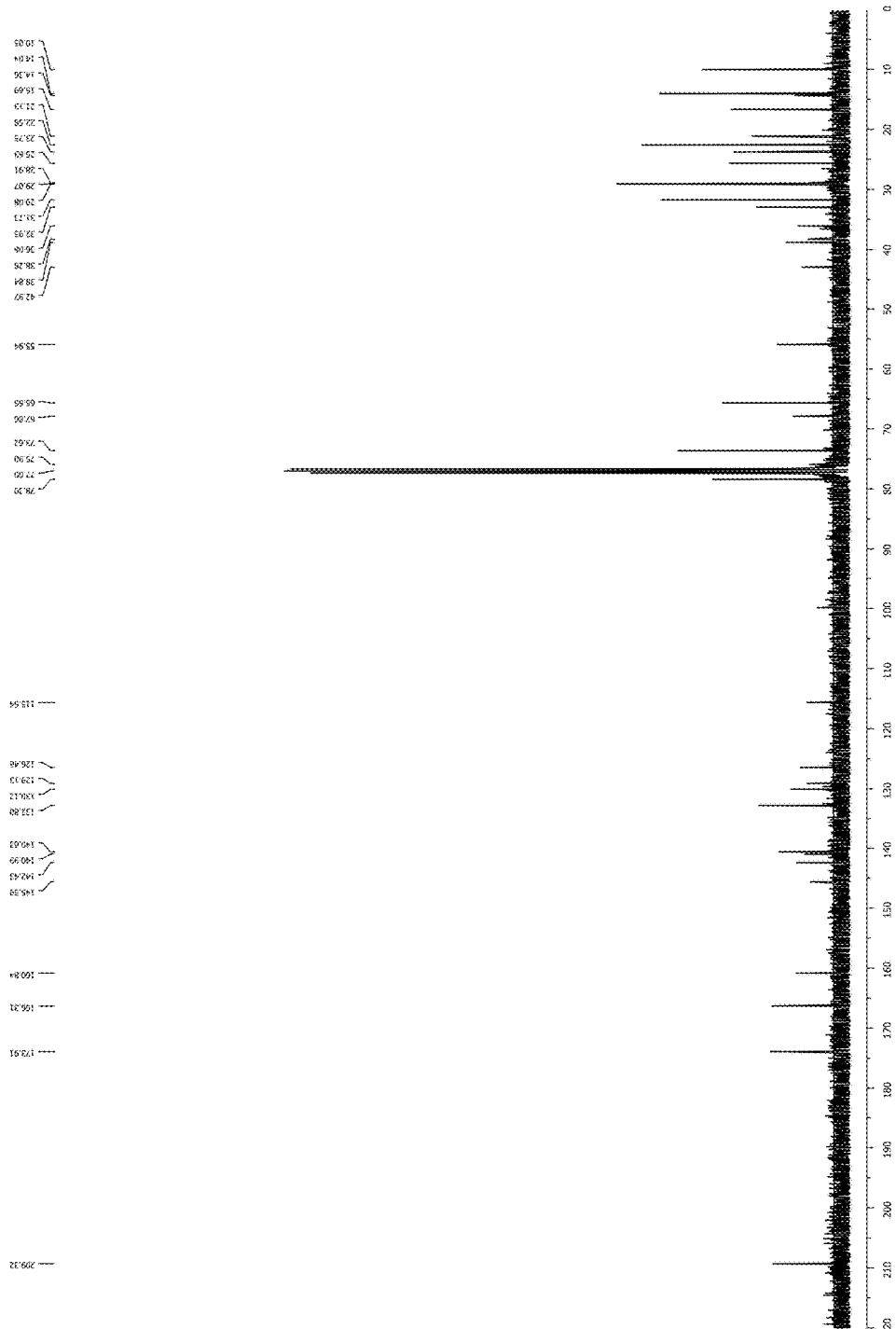
FIG. 6. shows $^{13}$C NMR spectrum of compound represented by Formula I.

In accordance with the preparation methods, phorbol ester I is 12-O-(2Z,4E,6E)-tetradeca-2,4,6-trienoylphorbol-13-acetate with a molecular formula of $C_{36}H_{50}O_8$ deduced from HRESIMS data m/z 633.33980 [M+Na]$^+$ (calcd for $C_{36}H_{50}O_8Na$, 633.33979); $[\alpha]^D_{25}$: $-3.75\pm1.97$ (c 0.0667, CHCl$_3$); UV (MeOH)$\lambda_{max}$ (log ε): 303 (2.78), 233 (2.75) nm; and IR (neat) $v_{max}$: 3413, 2965, 2922, 1710, 1615, 1377, 1258, 1092, 802 cm$^{-1}$. The $^1H$ and $^{13}C$ NMR spectra of phorbol ester I are shown in FIG. 5 and FIG. 6, respectively.

Figure 7:
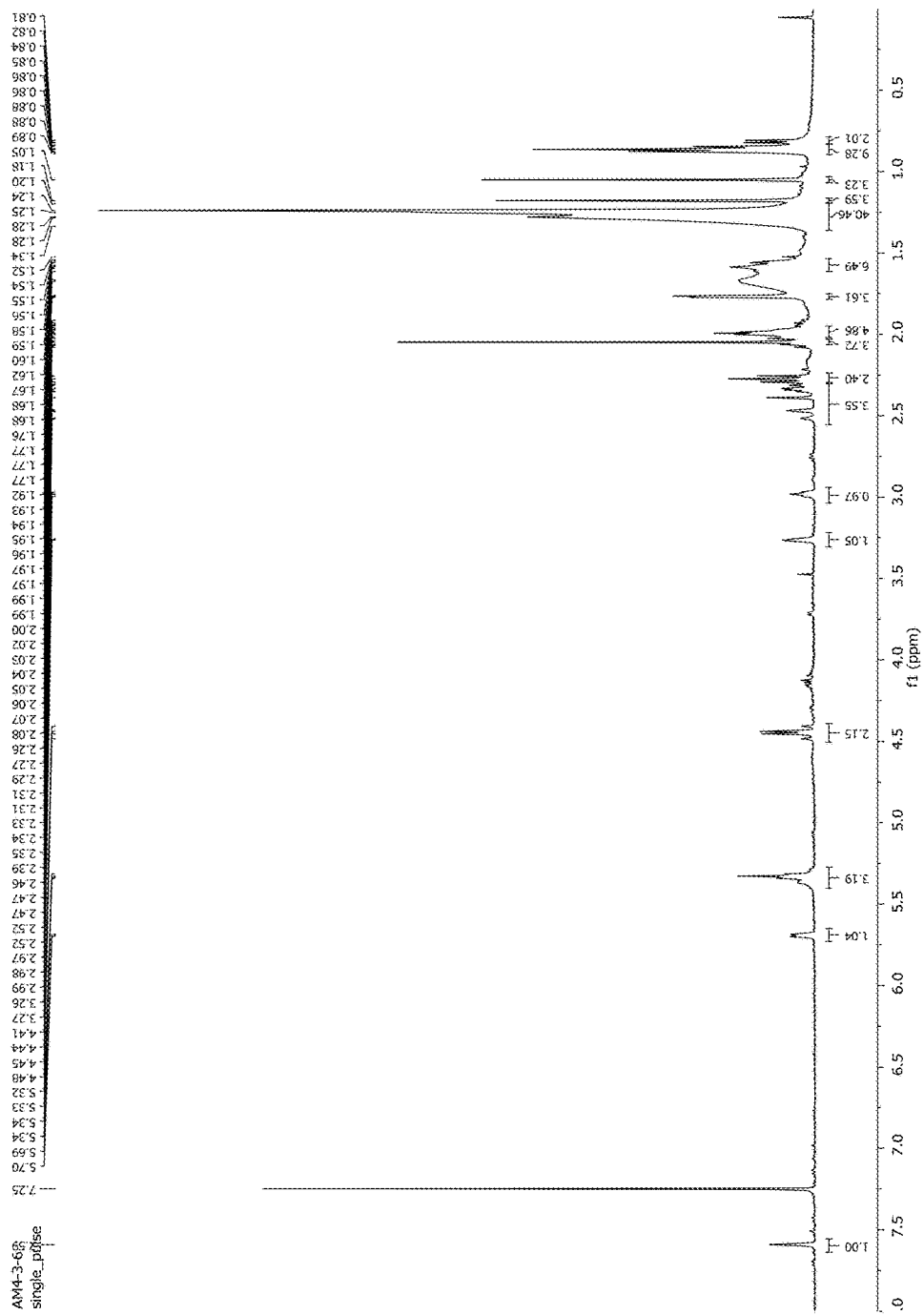
FIG. 7. shows $^1$H NMR spectrum of compound represented by Formula II.
Figure 8:
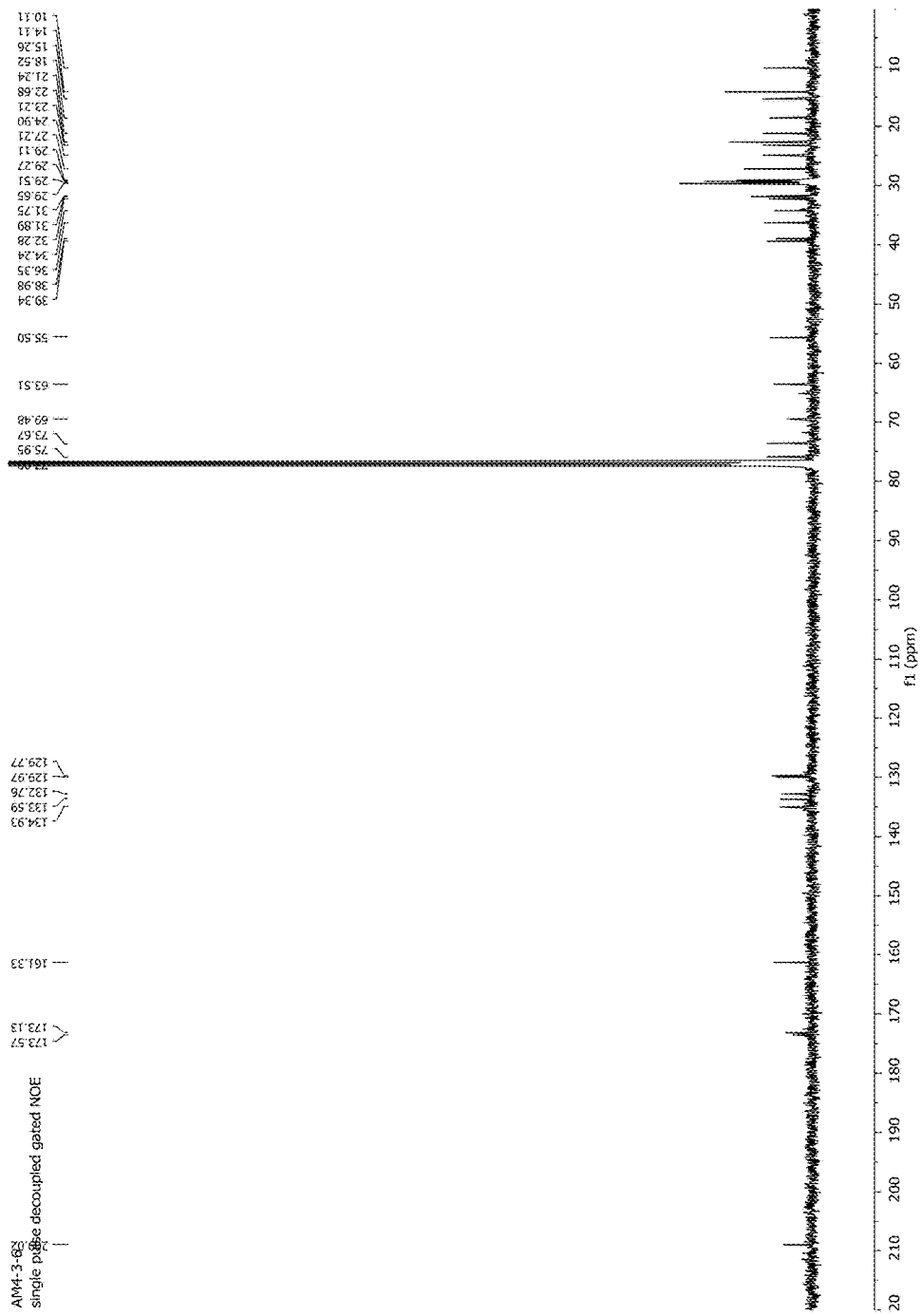
FIG. 8. shows $^{13}$C NMR spectrum of compound represented by Formula II.

In accordance with the preparation methods, phorbol ester II is 12-deoxy-13-O-acetoylphorbol-20-octadec-9-enoate with a molecular formula of $C_{40}H_{62}O_7$ deduced from HRESIMS data m/z 677.43884 [M+Na]$^+$ (calcd for $C_{40}H_{62}O_7Na$, 677.43878); $[\alpha]^D_{25}$: $+2.91\pm0.49$ (c 0.3333, CHCl$_3$); UV (MeOH) $\lambda_{max}$ (log ε): 285 (2.78), 250 (2.83) nm; and IR (neat) $v_{max}$: 3409, 2922, 2855, 1717, 1375, 1332, 1152, 1021 cm$^{-1}$. The $^1H$ and $^{13}C$ NMR spectra of phorbol ester II are shown in FIG. 7 and FIG. 8, respectively.

Figure 9:
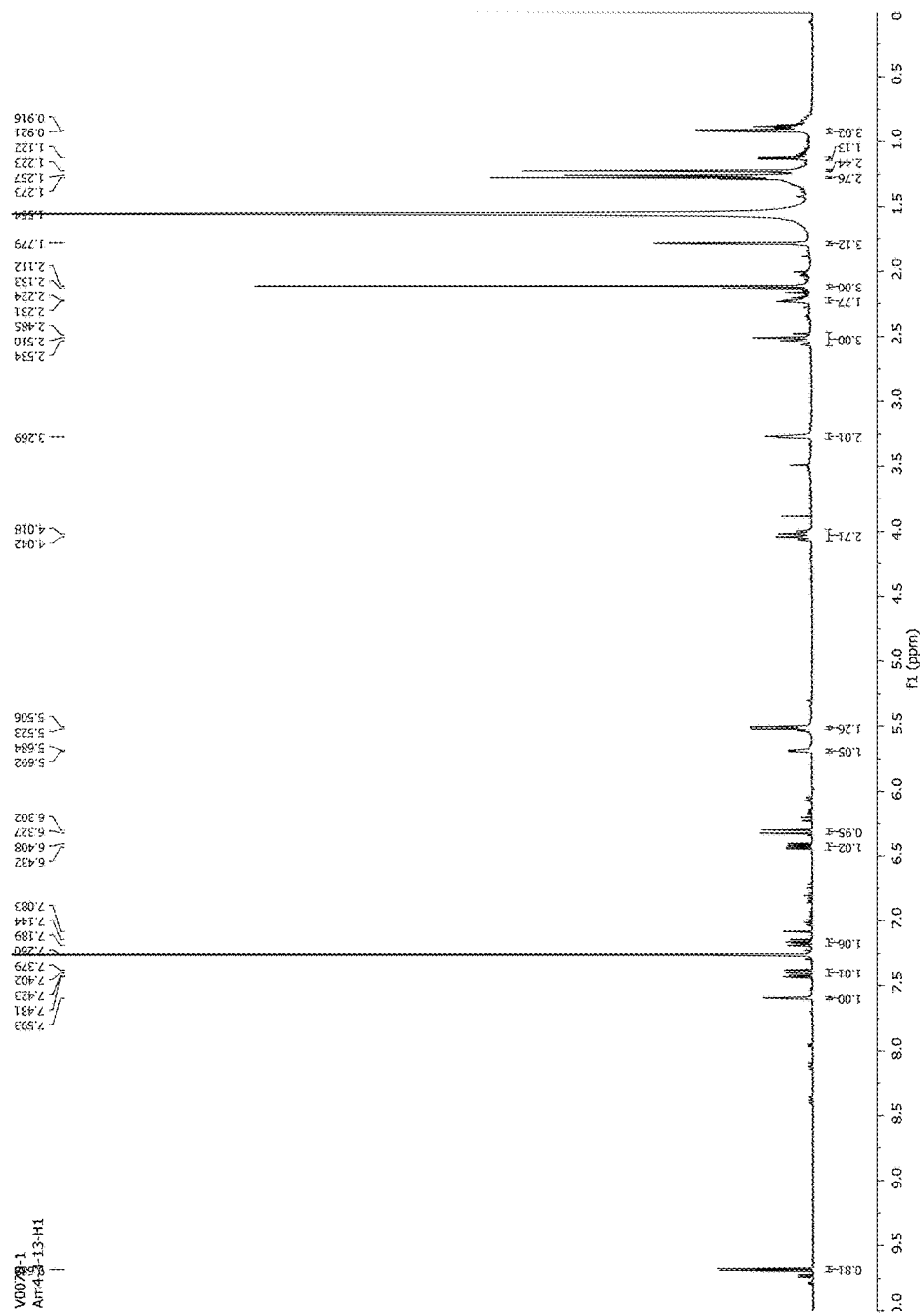
FIG. 9. shows $^1$H NMR spectrum of compound represented by Formula III.
Figure 10:
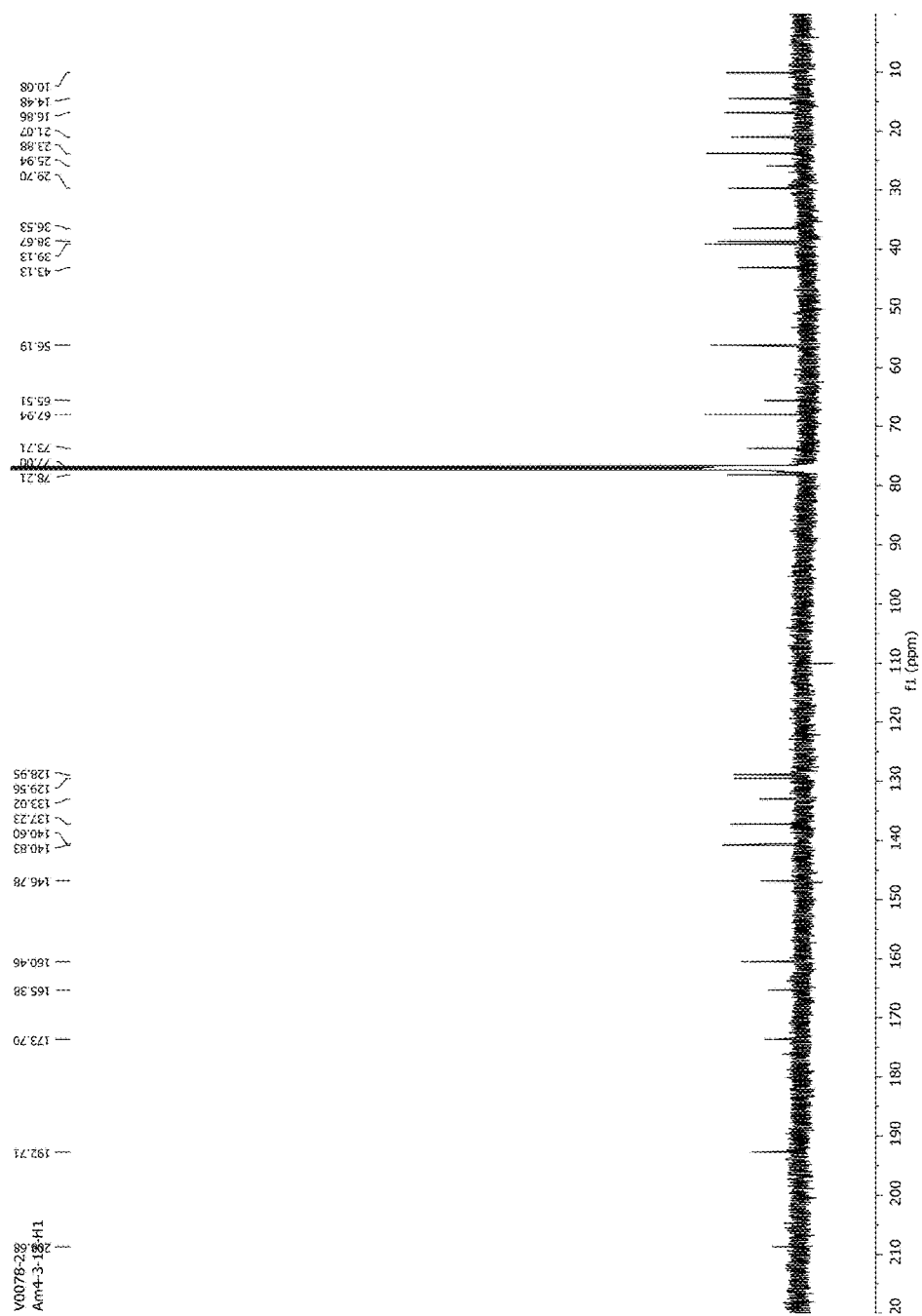
FIG. 10. shows $^{13}$C NMR spectrum of compound represented by Formula III.

In accordance with the preparation methods, phorbol ester III is 12-O-(2E,4E)-6-oxohexa-2,4-dienoylphorbol-13-acetate with a molecular formula of $C_{28}H_{34}O_9$ deduced from HRESIMS m/z 537.20959 [M+Na]$^+$ (calcd for $C_{28}H_{34}O_9Na$, 537.20950); $[\alpha]^D_{25}$: $+4.20\pm0.82$ (c 0.1667, CHCl$_3$); UV (MeOH) $\lambda_{max}$ (log ε): 295 (2.80), 249 (2.84) nm; and IR (neat) $v_{max}$: 3413, 2925, 2855, 2360, 2339, 1625, 1597, 1261, 1184, 755 cm$^{-1}$. The $^1H$ and $^{13}C$ NMR spectra of phorbol ester III are shown in FIG. 9 and FIG. 10, respectively.

Figure 11:
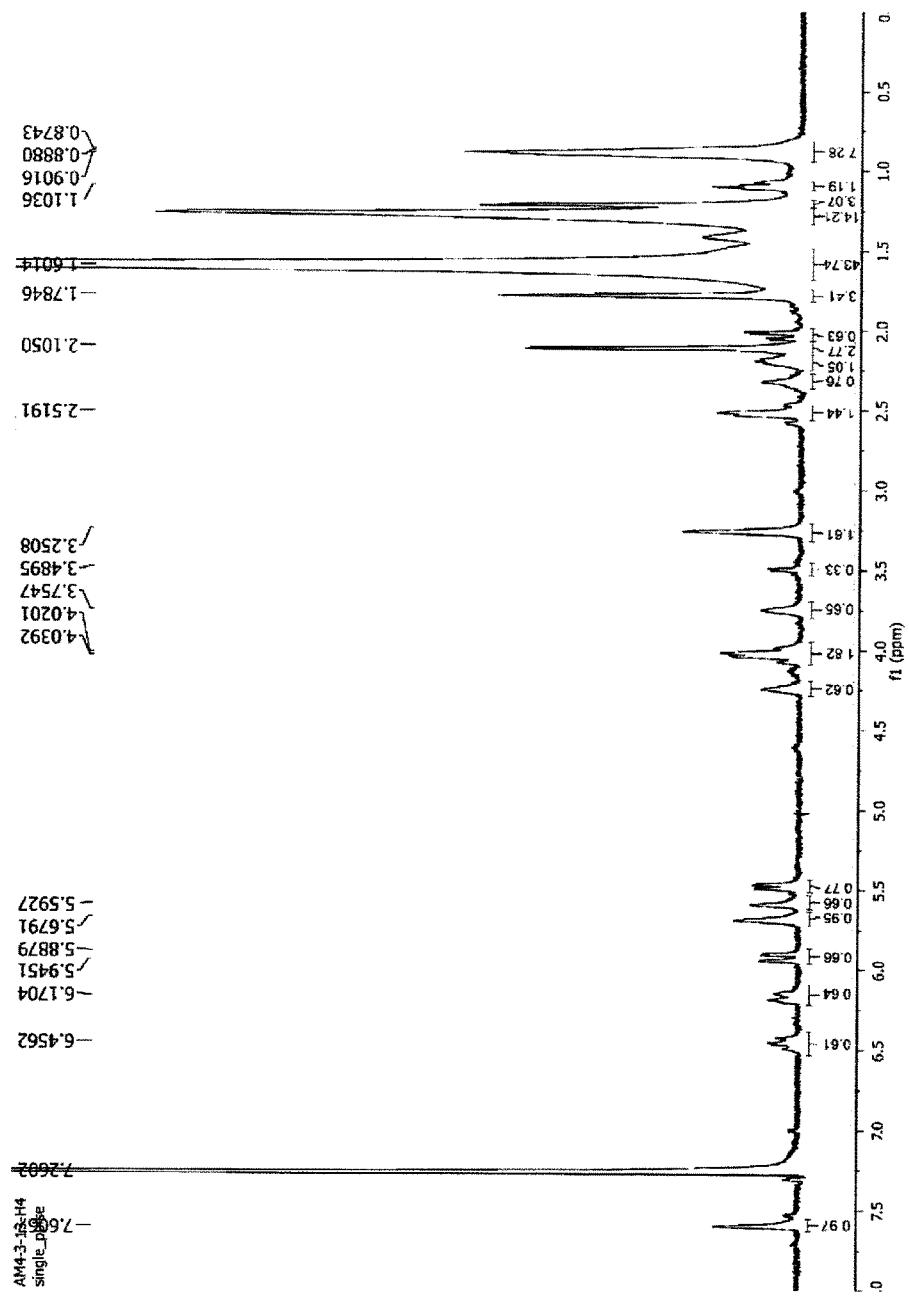
FIG. 11. shows $^1$H NMR spectrum of compound represented by Formula IV.
Figure 12:
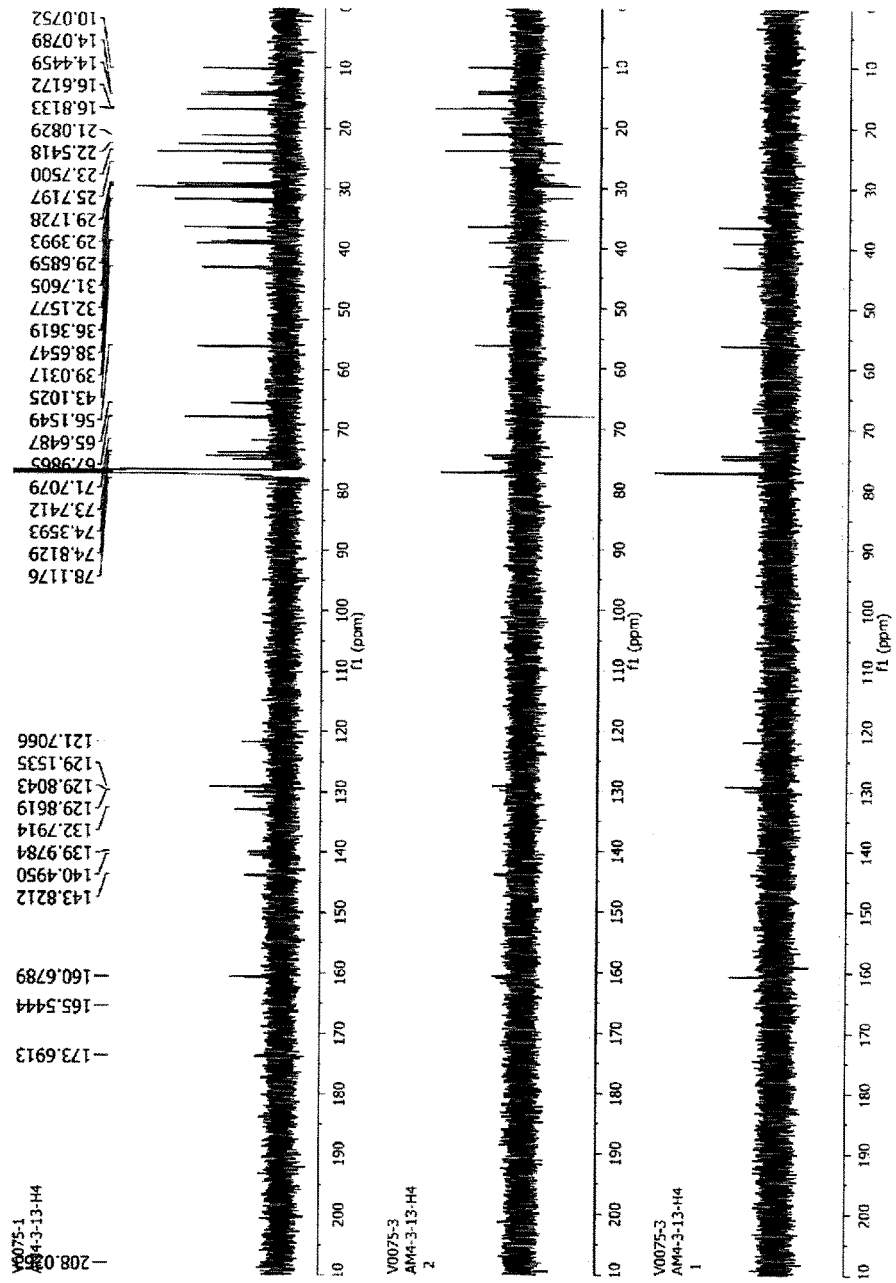
FIG. 12. shows $^{13}$C NMR spectrum of compound represented by Formula IV.

In accordance with the preparation methods, phorbol ester IV is 12-O-(2E,4E)-6,7-dihydroxytetradeca-2,4-dienoylphorbol-13-acetate with a molecular formula of $C_{36}H_{52}O_{10}$ deduced from HRESIMS m/z 667.34515 [M+Na]$^+$ (calcd for $C_{36}H_{52}O_{10}Na$, 667.34527); $[\alpha]^D_{25}$: +10.44±1.45 (c 0.1667, $CHCl_3$); UV (MeOH) $\lambda_{max}$ (log ε): 289 (2.79), 249 (2.83) nm; and IR (neat) $v_{max}$: 3392, 2925, 2851, 1710, 1632, 1455, 1375, 1261, 1024, 802, 755 cm$^{-1}$. The $^1H$ and $^{13}C$ NMR spectra of phorbol ester IV are shown in FIG. 11 and FIG. 12, respectively.

Figure 13:
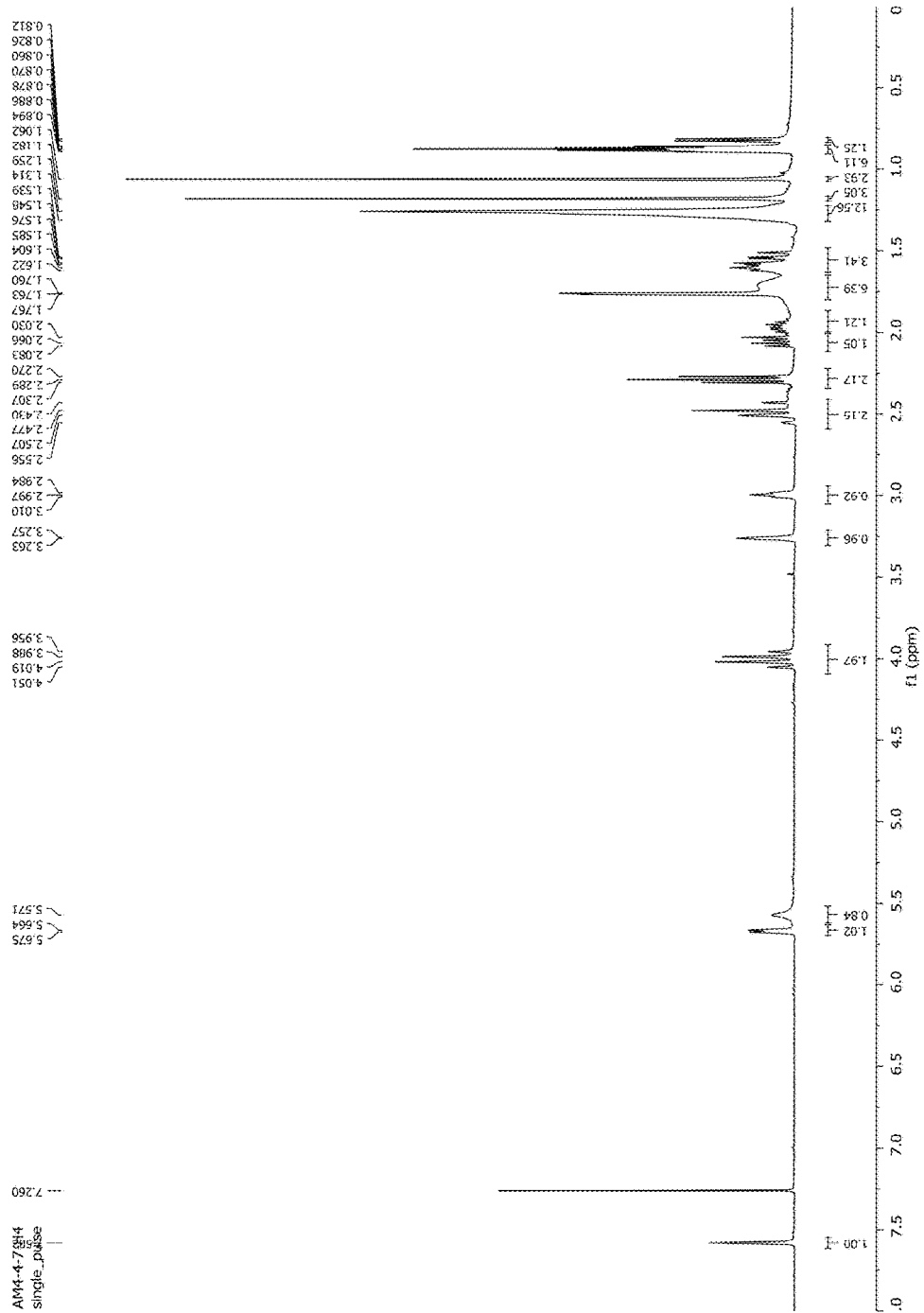
FIG. 13. shows $^1$H NMR spectrum of compound represented by Formula V.
Figure 14:
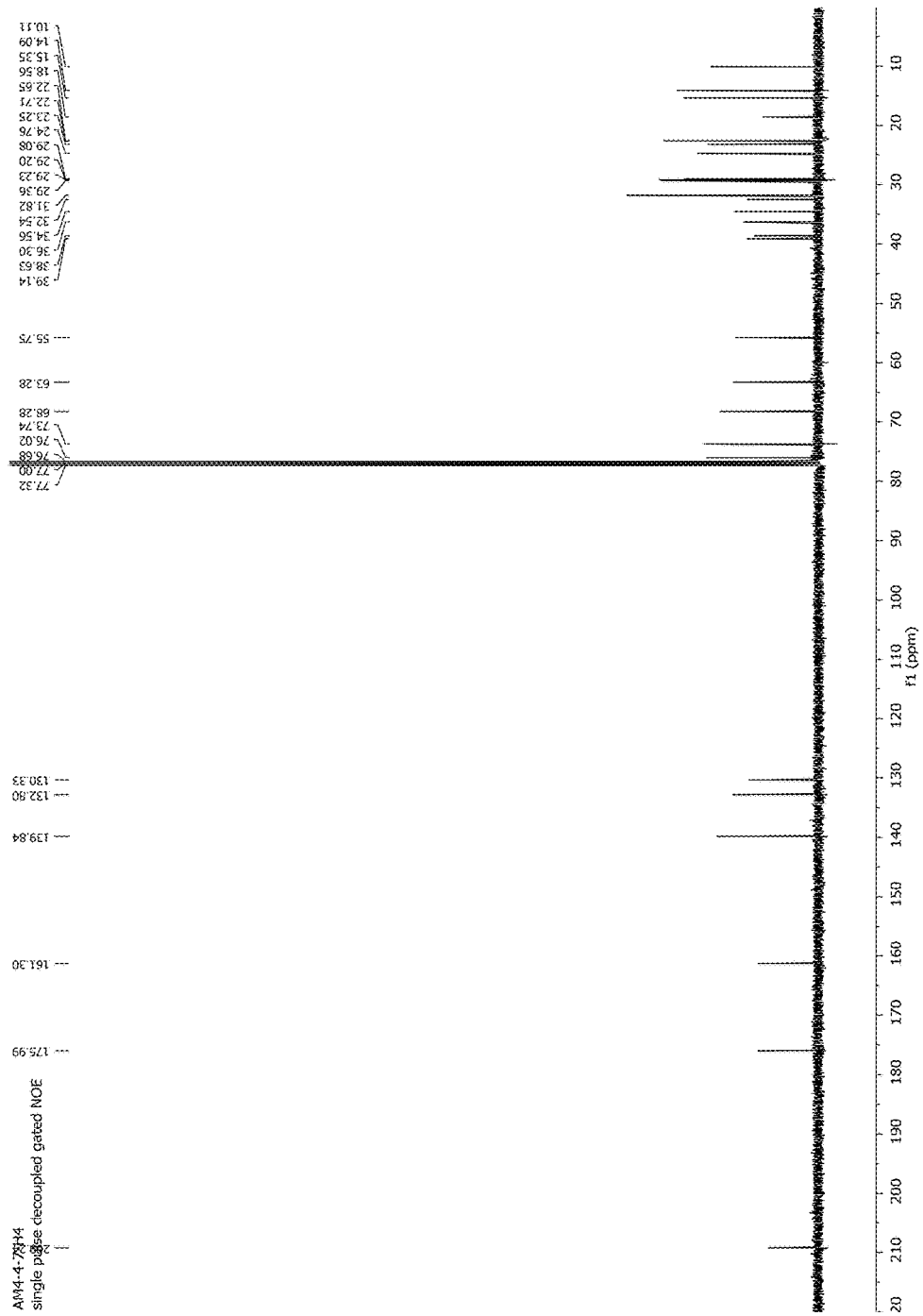
FIG. 14. shows $^{13}$C NMR spectrum of compound represented by Formula V.

In accordance with the preparation methods, phorbol ester V is 12-deoxyphorbol 13-decanoate with a molecular formula of $C_{30}H_{46}O_6$ deduced from HRESIMS m/z 525.31921 [M+Na]$^+$ (calcd for $C_{30}H_{46}O_6Na$, 525.31921); $[\alpha]^D_{25}$: +8.55±0.63 (c 0.200, $CHCl_3$); UV (MeOH) $\lambda_{max}$ (log ε): 325 (0.14), 249 (1.31) nm; and IR (neat) $v_{max}$: 3392, 2925, 2356, 1710, 1629, 1335, 1155 cm$^{-1}$. The $^1H$ and $^{13}C$ NMR spectra of phorbol ester V are shown in FIG. 13 and FIG. 14, respectively.

Figure 15:
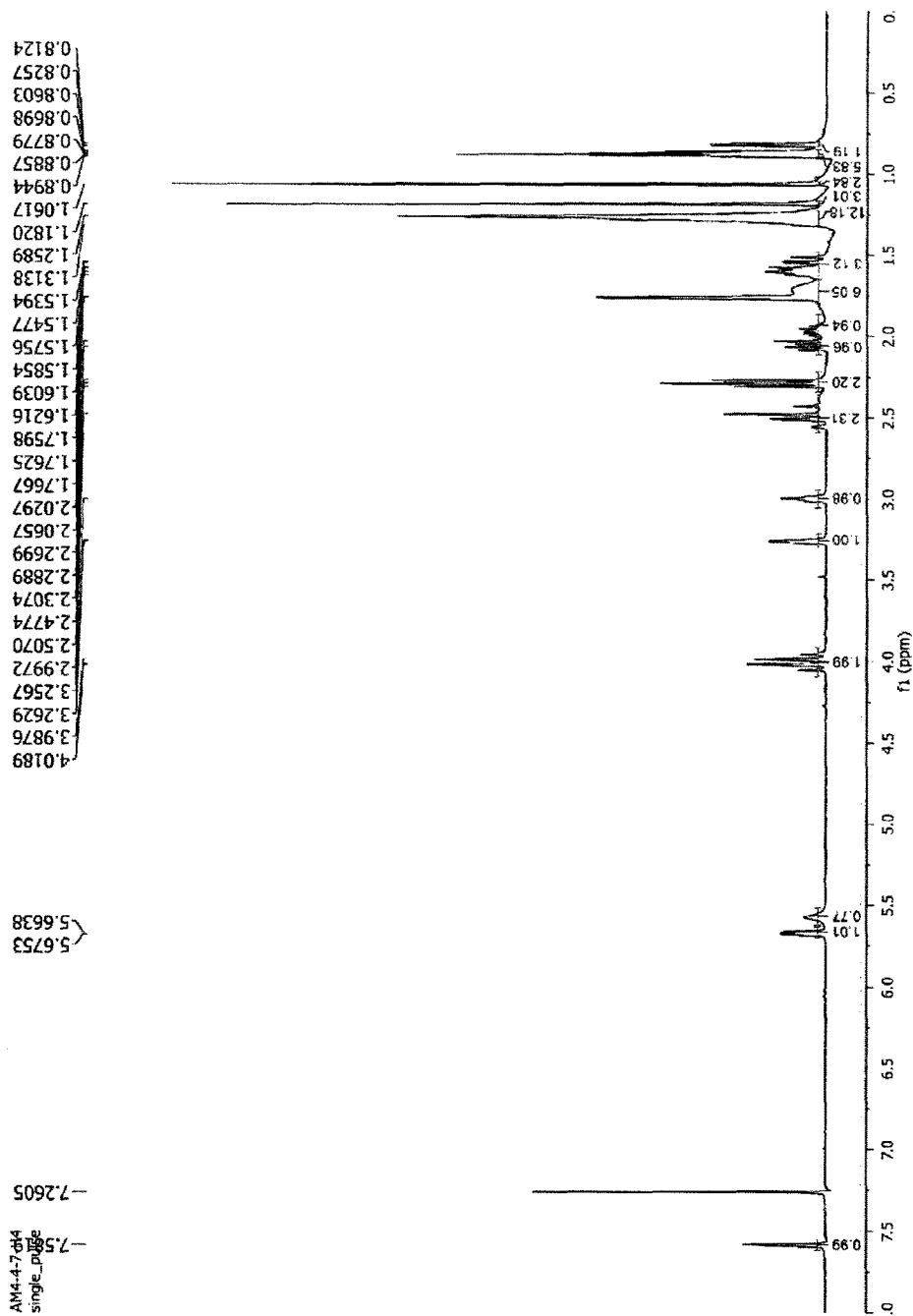
FIG. 15. shows $^1$H NMR spectrum of compound represented by Formula VI.
Figure 19:
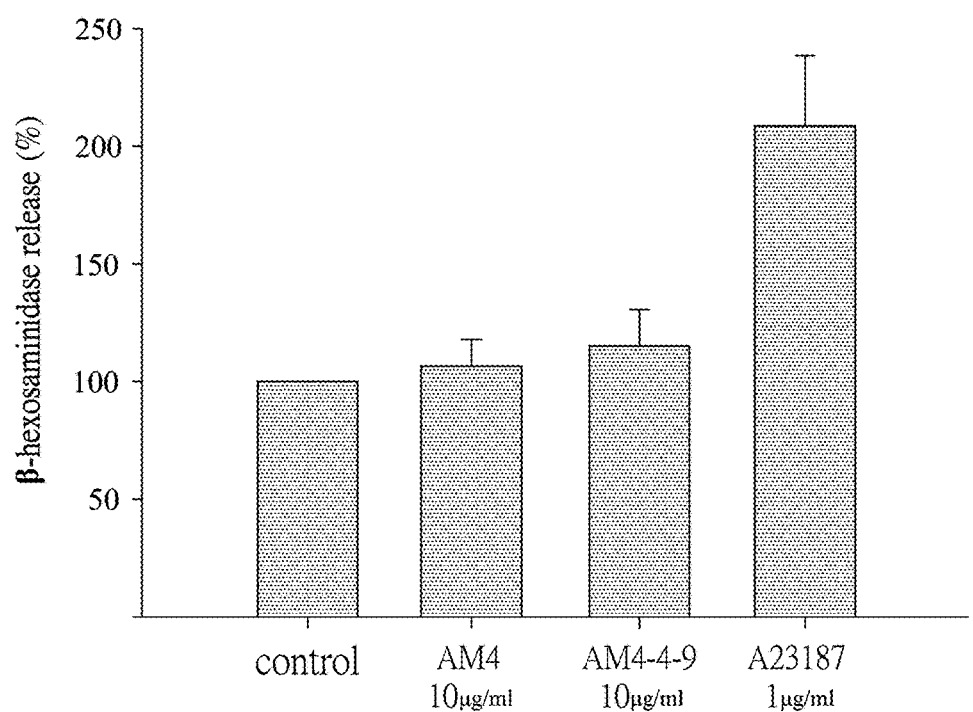
FIG. 19. shows Activity of phorbol ester-rich fraction (AM4) and phorbol ester I on stimulant-free degranulation in RBL-2H3 cells.

In accordance with the preparation methods, phorbol ester VI is 12-deoxyphorbol 13-octanoate with a molecular formula of $C_{28}H_{42}O_6$ deduced from ESIMS m/z 475 [M+H]$^+$ (calcd for $C_{28}H_{43}O_6$); $[\alpha]^D_{25}$: +4.75±1.27 (c 0.200, $CHCl_3$); UV (MeOH) $\lambda_{max}$ (log ε): 311 (0.01), 250 (2.85) nm; and IR (neat) $v_{max}$: 3377, 2922, 2858, 1710, 1625, 1332, 1018 cm$^{-1}$. The $^1H$ NMR spectrum of phorbol ester VI is shown in FIG. 15.

In the present specification and the scope of the patent application, the provided chemicals with formulas I~VI should comprise all of their optical isomers and stereoisomers, therefore, all of these optical and stereo isomers are included within the scope of the present invention.

For the proposes of this invention, the compositions of antiallergic phorbol ester and phorbol derivatives as the main active ingredients from the seeds of *Aquilaria malaccensis* were evaluated by the following assays.

Cell culture: The mucosal mast cell-derived rat basophilic leukemia (RBL-2H3) cell line was purchased from the Bioresource Collection and Research Center (Hsin-Chu, Taiwan). Cells were grown in DMEM medium supplemented with 10% FBS and 100 U/mL penicillin plus 100 μg/mL streptomycin. Cells were cultured in 10 cm cell culture dishes at 37° C. in a humidified chamber with 5% $CO_2$ in air.

Sample preparations: In accordance with the preparation methods of this invention, the compositions from the seeds of *Aquilaria malaccensis*, the ethanolic extract (EtOH), n-butanol layer (BuOH), aqueous layer (Water), ethyl acetate layer (EtOAc), n-hexane layer (Hexane), 90% aqueous methanol layer (MeOH), the divided AM-4, AM4-4-7, AM4-4-8, AM4-4-9 (phorbol ester I), were prepared for bioactive assays.

Cell viability assay: A methylthiazol tetrazolium (MTT) assay was used to measure the potential toxic effects of the samples on RBL-2H3 cells (Chen et al., J. Nat. Prod., 72, 950-953, 2009). Briefly, RBL-2H3 cells (2×104 cells/well) were seeded in a 96-well plate overnight and treated with various concentrations of samples (10~100 μg/mL) for 24 h. MTT solution (0.5 mg/mL) was added to the wells (80 μL per well) and incubated for 1 h. The formed formazan crystals were dissolved in DMSO (80 μL). The absorbance at 595 nm was measured using microplate reader (Multiskan Ascent, Thermo Scientific). The degree of cell viability of each sample was calculated as the percentage of control value (untreated cells). The maximal tolerated dose of DMSO was 0.5%. All experiments were repeated at least two times.

Degranulation β-hexosaminidase assay induced by A23187 or antigen: The degree of A23187- and antigen-induced degranulation in RBL-2H3 cells was determined by a β-hexosaminidase release assay as described previously (Chen et al., J. Nat. Prod., 72, 950-953, 2009; Matsuda et al., Bioorg. Med. Chem., 12, 5891-5898, 2004) with following modifications. RBL-2H3 cells were seeded in a 96-well plate (2×10$^4$ cells/well) for A23187-induced and in 48-well plate (3×10$^4$ cells/well) for antigen-induced experiment. Cells were treated with various concentrations of the samples for 20 h. Dexamethasone (10 nM) was used as a positive control. The cells for the antigen-induced experiment were first sensitized with anti-DNP IgE (5 μg/mL) for at least 2 h. After thorough washing by pre-warmed Tyrode's buffer (135 mM NaCl, 5 mM KCl, 1.8 mM $CaCl_2$, 1.0 mM $MgCl_2$, 5.6 mM glucose, 20 mM HEPES at pH 7.4), the cells were stimulated by either calcium ionophore A23187 (1 μM) or antigen DNP-BSA (100 ng/mL) in Tyrode's buffer for 1 h. Unstimulated cells were either lysed with 0.5% Triton X-100 solution for the total amount of β-hexosaminidase release or left untreated for spontaneous release of β-hexosaminidase. Then aliquots of supernatants (50 μL) were incubated with equal volume of 1 μM of p-NAG (50 μL) prepared in 0.1 M citrate buffer (pH 4.5) serving as a substrate for the released β-hexosaminidase. After 1 h of incubation at 37° C., the reaction was quenched by the addition of 100 μL of stop buffer (0.1 M Na2/NaHCO3, pH 10.0). Absorbance was measured at 405 nm on a microplate reader (Multiskan Ascent, Thermo Scientific). The inhibition percentage of β-hexosaminidase release was calculated as the percentage of control value (untreated stimulated cells). The maximal tolerated dose of DMSO was 0.5%. All experiments were repeated three times.

Effect on enzymatic activity of β-hexosaminidase: To test the possible effect of the sample on enzymatic activity, following assay was performed. The cell suspension (2×10$^6$ cells) in 2 mL of Tyrode's buffer was sonicated for 5 min. The solution was then centrifuged, and the supernatant was diluted with 8 mL of Tyrode's buffer. The enzyme solution (45 μL) and test sample solution (5 μL) were transferred into a 96-well microplate and enzyme activity was examined as described above (the section of Cell viability assay). All experiments were repeated three times.

Direct degranulation β-hexosaminidase assay induced by the sample: The degree of β-hexosaminidase release triggered by the sample in RBL-2H3 cells was determined by a modified β-hexosaminidase release assay. Briefly, RBL-2H3 cells (4×10$^4$ cells/well) were seeded in a 48-well plate and treated with the samples for 10 h. Tyrode's buffer supplemented with 5.6 mM glucose, 2 mg/mL BSA and 2 mM glutamine was used to prepare the samples and treat the cells. Then 50 μL of supernatants were transferred into a 96-well microplate and examined as described above (the section of Cell viability assay). A23187 (1 μM) was used as a positive control. All experiments were repeated three times.

Preparation of human neutrophils: Human neutrophils from venous blood of healthy, adult volunteers (20-30 years old) were isolated using a standard method of dextran sedimentation prior to centrifugation in a Ficoll-Hypaque gradient and hypotonic lysis of erythrocytes (Boyum et al., Scand. J. Clin. Lab. Invest., 97, 77-89, 1968). Purified neutrophils containing >98% viable cells, as determined by the trypan-blue exclusion method (Jauregui et al., In Vitro, 17, 1100-1110, 1981), were resuspended in a $Ca^{2+}$-free Hank's buffered salt solution (HBSS) at pH 7.4 and were maintained at 4° C. prior to use.

Superoxide anion generation assay and elastase release inhibition assay: Neutrophil superoxide anion generation was determined using superoxide dismutase (SOD)-inhibitory cytochrome reduction according to described procedures (Babior et al., J. Clin. Invest., 52, 741-744, 1973; Hwang et al., Free Radical Bio. Med., 41, 1433-1441, 2006). Degranulation of azurophilic granules was determined by measuring the elastase release as described previously (Hwang et al., Free Radical Bio. Med., 41, 1433-1441, 2006). All experiments were repeated at least three times.

Cytotoxic assay: MTT assay was used to according to the used in a previous manuscript. HepG2 ($1\times10^4$ cells), $A549$ ($5\times10^3$ cells), and MDA-MB-231 ($1\times10^4$ cells) were seeded into 96-well plates, followed by treatment with the AMS samples at concentration of 20 μg/mL After 72 h, the medium was removed and 100 μL of MTT solution (0.5 mg/mL) was added to each well. The plates were then incubated at 37° C. for 1 h and then, the MTT dye was detected by the addition of DMSO (100 μL). The absorbance was recorded at 550 nm. Doxorubicin was used as a positive control.

In accordance with the assays, antiallergic activity of the compositions from *Aquilaria malaccensis* seeds and A23187 (a positive control) was concluded in Table 1 whereas antiinflammatory effects of the compositions from *A. malaccensis* seeds on superoxide anion generation and elastase release in fMLP/CB-induced human neutrophils were summarized in Table 2. Furthermore, activity of phorbol ester-rich fraction (AM4) and phorbol ester I on stimulant-free degranulation in RBL-2H3 cells was shown in Table 4. The RBL-2H3 cells were treated with AM4 (10 μg/ml) and phorbol ester I (10 μg/ml) for 10 h. In the stimulant-free degranulation assay, Tyrode's buffer supplemented with glucose, bovine serum albumin (BSA) and glutamine was used as a medium. A23187 (1 μM) was used as a positive control.

In accordance with antiallergic activity of the compositions from *Aquilaria malaccensis* seeds (Table 1), the ethanolic extract (A-EtOH) showed potent antiallergic activity ($IC_{50}$ 0.92 and 3.9 μg/mL in A23187 and antigen-induced β-hexosaminidase assay, respectively. To clarify that antiallergic activity of the samples was due to inhibition of β-hexosaminidase release, and not false positive as a result of direct inhibition of β-hexosaminidase enzymatic activity (Wang et al., Biol. Pharm. Bull., 30, 388-392, 2007), the enzyme was extracted and tested with the active samples. None of the samples inhibited the enzymatic activity of β-hexosaminidase. As the methanol layer (A-MeOH) proved the best antiallergic activity ($IC_{50}$ 0.0089 and 0.069 μg/mL in A23187 and antigen-induced degranulation assay, respectively), it was further separated using silica gel column chromatography to yield six fractions, AM1~AM6. Among them, fraction AM4 showed the most remarkable antiallergic activity inhibiting β-hexosaminidase release from mast cells induced by either $A23187$ ($IC_{50}$ 0.0034 μg/mL) or antigen ($IC_{50}$ 0.0065 μg/mL).

In accordance with antiinflammatory effects of the compositions from *Aquilaria malaccensis* seeds on superoxide anion generation and elastase release in fMLP/CB-induced human neutrophils (Table 2), the ethanolic extract (A-EtOH) showed antiinflammatory activity (90.1% and 85.3% inhibition of superoxide generation and elastase release at 10 μg/mL, respectively). All partitioned fractions except the water layer (A-Water) displayed significant antiallergic and antiinflammatory activities.

In accordance with cytotoxic activities of the compositions from *Aquilaria malaccensis* seeds against HepG2, MDA-MB231, and $A549$ carcinoma cell lines (Table 3), only some of the compositions showed cytotoxic activities at 20 μg/mL level, (A-BuOH 57.1% against A549, AM4 56.5% against MDA-MB231 and 79.3% against A549, AM6 56.0% against MDA-MB231 cell line). Moreover, considering weak cytotoxicity of the compositions towards RBL-2H3 cells, the antiallergic active fraction AM4 exerted therapeutic index up to 28000. To further rule out the possibility that AM4 causes direct mast cell activation, we examined the capacity of AM4 to elicit degranulation by itself. Results showed that the AM4 treatments did not cause significant degranulation as compared with untreated control (Table 1).

Particularly, in accordance with antiallergic activity of the compositions from *Aquilaria malaccensis* seeds (Table 1), AM4-4 ($IC_{50}$ $4.8\times10^{+5}$ μg/mL, therapeutic index 1477328, $A23187$-induced; and $IC_{50}$ $6.8\times10^{+4}$ μg/mL, therapeutic index 103776, antigen-induced (β-hexosaminidase assay) afforded the most active fraction AM4-4-8 ($IC_{50}$ $7.6\times10^{-6}$ μg/mL, therapeutic index 9645374, A23187-induced; and $IC_{50}$ $8.0\times10^{+5}$ μg/mL, therapeutic index 9645374, antigen-induced degranulation assay), and a new compound, phorbol ester I ($IC_{50}$ values of 0.0017 μM, therapeutic index 71538, A23187-induced; and $IC_{50}$ 0.011 μM, therapeutic index 10550, antigen-induced degranulation assay).

In accordance with the above bioactive results in this invention, the phorbol ester I really possesses the antiallergic activity and can be pharmaceutically applied for preventing and treating allergies. Similarly, AM4-4-9 subfraction comprising phorbol ester I also really possesses the antiallergic activity and can be pharmaceutically applied for preventing and treating allergies. Therefore, AM4-3-13, AM4-4-3, and AM4-4-7 subfractions have the antiallergic activity correspondingly. In accordance with the results of this invention, the extractions and the fractionated fractions (phorbol ester-contained fractions) from *Aquilaria malaccensis* seeds can be pharmaceutically applied for preventing and treating allergies and show the potent antiallergic activity.

REFERENCES

1. Lian, Q.; Cheng, Y.; Zhong, C.; Wang, F. "Inhibition of the IgE-mediated activation of RBL-2H3 cells by TIPP, a novel thymic immunosuppressive pentapeptide." Int. J. Mol. Sci., 16, 2252-2268 (2015).

2. Dearman, R. J.; Skinner, R. A.; Deakin, N.; Shaw, D.; Kimber, I. "Evaluation of an in vitro method for the measurement of specific IgE antibody responses: The rat basophilic leukemia (RBL) cell assay." Toxicology, 206, 195-205 (2005).
3. Talukdar, A. "Gas chromatography-mass spectrometric analysis of the essential oil of eaglewood (*Aquilaria agalloocha* Roxb)." Int. J. Pharm. Pharm. Sci., 6, 629-631 (2014).
4. Yang, L.; Qiao, L.; Ji, C.; Xie, D.; Gong, N.-B.; Lu, Y.; Zhang, J.; Dai, J.; Guo, S. "Antidepressant abietane diterpenoids from Chinese eaglewood." J. Nat. Prod., 76, 216-222 (2013).
5. Huong, D. T. L.; Dat, N. T.; Minh, C. V.; Kang, J. S.; Kim, Y. H. "Monoamine oxidase inhibitors from *Aquilaria agallocha*." Nat. Prod. Sci., 8, 30-33. (2002).
6. Huo, H.-X.; Zhu, Z.-X.; Pang, D.-R.; Li, Y.-T.; Huang, Z.; Shi, S.-P.; Zheng, J.; Zhang, Q.; Zhao, Y.-F.; Tu, P.-F. "Anti-neuroinflammatory sesquiterpenes from Chinese eaglewood." Fitoterapia, 106, 115-121 (2015).
7. Zhou, M.; Wang, H.; Suolangjiba; Kou, J.; Yu, B. "Antinociceptive and anti-inflammatory activities of *Aquilaria sinensis* (Lour.) Gilg. leaves extract." J. Ethnopharmacol., 117, 345-350 (2008).
8. Kamonwannasit, S.; Nantapong, N.; Kumkrai, P.; Luecha, P.; Kupittayanant, S.; Chudapongse, N. "Antibacterial activity of *Aquilaria crassna* leaf extract against *Staphylococcus epidermidis* by disruption of cell wall." Ann. Clin. Microbiol. Antimicrob., 12, 20 (2013).
9. Pranakhon, R.; Aromdee, C.; Pannangpetch, P. "Effects of iriflophenone 3-C-β-glucoside on fasting blood glucose level and glucose uptake." Pharmacogn. Mag., 11, 82-89 (2015).
10. Hara, H.; Ise, Y.; Morimoto, N.; Shimazawa, M.; Ichihashi, K.; Ohyama, M.; Iinuma, M. "Laxative effect of agarwood leaves and its mechanism." Biosci. Biotechnol. Biochem., 72, 335-345 (2008).
11. Pant, P.; Rastogi, R. P. "Agarol, a new sesquiterpene from *Aquilaria agallocha*." Phytochemistry, 19, 1869-1870 (1980).
12. Gunasekera, S. P.; Kinghorn, A. D.; Cordell, G A.; Farnsworth, N. R. "Plant anticancer agents. XIX. Constituents of *Aquilaria malaccensis*." J. Nat. Prod., 44, 569-572 (1981).
13. Dyary, H. O.; Arifah, A. K.; Sharma, R. S.; Rasedee, A.; Mohd-Aspollah, M. S.; Zakaria, Z. A.; Zuraini, A.; Somchit, M. N. "Antitrypanosomal screening and cytotoxic effects of selected medicinal plants." Trop. Biomed., 31, 89-96 (2014).
14. Dash, M.; Patra, J. K.; Panda, P. P. "Phytochemical and antimicrobial screening of extracts of *Aquilaria agallocha* Roxb." Afr. J. Biotechnol., 7, 3531-3534 (2008).
15. Kim, Y. C.; Lee, E. H.; Lee, Y. M.; Kim, H. K.; Song, B. K.; Lee, E. J.; Kim, H. M. "Effect of the aqueous extract of *Aquilaria agallocha* stems on the immediate hypersensitivity reactions." J. Ethnopharmacol., 58, 31-38 (1997).
16. Chen, B. H., Wu, P. Y., Chen, K. M., Fu, T. F., Wang, H. M., Chen, C. Y. "Antiallergic potential on RBL-2H3 cells of some phenolic constituents of *Zingiber officinale* (ginger)." J. Nat. Prod., 72, 950-953 (2009).
17. Matsuda, H., Tewtrakul, S., Morikawa, T., Nakamura, A., Yoshikawa, M. "Anti-allergic principles from Thai zedoary: Structural requirements of curcuminoids for inhibition of degranulation and effect on the release of TNF-α and IL-4 in RBL-2H3 cells." Bioorg. Med. Chem., 12, 5891-5898 (2004).
18. Boyum, A. "Isolation of mononuclear cells and granulocytes from human blood." Scand. J. Clin. Lab. Invest., 97, 77-89 (1968).
19. Jauregui, H. O., Hayner, N. T., Driscoll, J. L., Williams-Holland, R., Lipsky, M. H., Galletti, P. M. "Trypan blue dye uptake and lactate dehydrogenase in adult rat hepatocytes-freshly isolated cells, cell suspensions, and primary monolayer cultures." In Vitro, 17, 1100-1110 (1981).
20. Babior, B. M., Kipnes, R. S., Curnutte, J. T. "Biological defense mechanisms. The production by leukocytes of superoxide, a potential bactericidal agent." J. Clin. Invest., 52, 741-744 (1973).
21. Hwang, T. L., Leu, Y. L., Kao, S. H., Tang, M. C., Chang, H. L. "Viscolin, a new chalcone from Viscum coloratura, inhibits human neutrophil superoxide anion and elastase release via a cAMP-dependent pathway." Free Radical Bio. Med., 41, 1433-1441 (2006).
22. Wang, Q.; Matsuda, H.; Matsuhira, K.; Nakamura, S.; Yuan, D.; Yoshikawa, M "Inhibitory effects of thunberginols A, B, and F on degranulations and releases of TNF-alpha; and IL-4 in RBL-2H3 cells." Biol. Pharm. Bull., 30, 388-392 (2007).

Outstandingly, this invention is characteristic for the advantages of easy collection, simple procedure, and plant growth no-effect due to the phorbol esters preparations from the seeds of *Aquilaria malaccensis* rather than the stems and barks. Besides, in accordance with the preparation methods of this invention, four new phorbol esters I~IV were isolated.

This invention is unprecedented and filled with novelty and progressiveness, thus it is prudential to meet the requirement invention patents, and the patent application is made according to the law.

All above described is used only for illustrating possible embodiments of the present invention, and therefore it can not limit the protection scope of this invention. All skilled equal changes or modifications in accordance with the present invention are still under the terms of the specification and the scope of the present invention.

We claim:

1. A method for preparing compositions from *Aquilaria malaccensis* seeds, the method including the following steps:
    (a) extracting *Aquilaria malaccensis* seeds that are air dried and powdered with 90% ethanol at room temperature in triplicate and concentrating the extract under a reduced pressure to provide an ethanolic extract;
    (b) partitioning the ethanolic extract by suspending the ethanolic extract in water, followed by partitioning carried out with equivalent ethyl acetate in triplicate, so as to separate an organic ethyl acetate layer;
    (c) subjecting the ethyl acetate layer to partitioning with n-hexane and 90% aqueous methanol (MeOH) to obtain a hexane layer and a MeOH layer;

(d) subjecting the MeOH layer to column chromatography over silica gel under gradient elution of n-hexane/$CH_2Cl_2$/MeOH of 6:3:1, 6:4:1, 6:6:1, 6:8:1, 6:10:1 and 5:10:2 to yield six respective fractions of AM1, 6:3:1; AM2, 6:4:1; AM3, 6:6:1; AM4, 6:8:1; AM5, 6:10:1; and AM6, 6:10:2;

(e) fractioning fraction AM4 over a dextran bead sizing column with a ratio of $CH_2Cl_2$/MeOH being 1:1 to obtain eight sub-fractions, which are respectively AM4-1 to AM4-8;

(f) subjecting fraction AM4-3 to column chromatography over silica under gradient elution of EtOAc/n-hexane from 1:10 to, 4:1 to obtain fifteen AM4-3 originating subfractions, which are respectively AM4-3-1 to AM4-3-15; and (g) separating fraction AM4-4 with column chromatography on silica gel under gradient elution of EtOAc/n-hexane from 1:15 to 4:1 to obtain twelve AM4-4 originating subfractions, which are respectively AM4-4-1 to AM4-4-12, wherein the fifteen AM4-3 originating subfractions and the twelve AM4-4 originating subfractions are further separated on column chromatography over silica gel to provide phorbol esters of the following formulas:

Formula I: 12-O-(2Z,4E,6E)-tetradeca-2,4,6-trienoyl-phorbol-13-acetate having a molecular formula $C_{36}H_{50}O_8$ of structural formula:

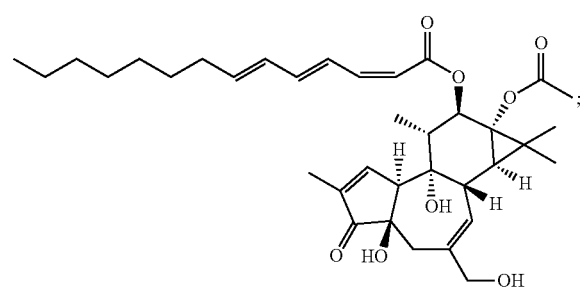

Formula II: 12-deoxy-13-O-acetoylphorbol-20-octadec-9-enoate having a molecular formula $C_{40}H_{62}O_7$ of structural formula:

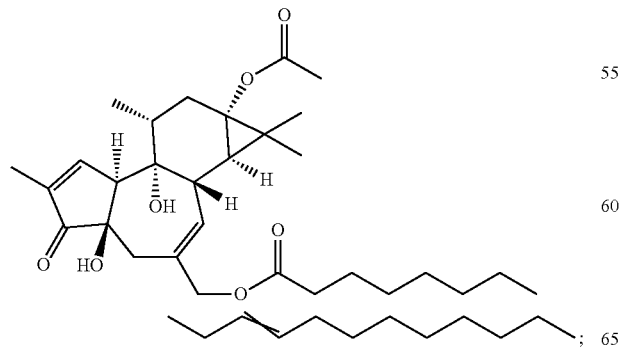

Formula III: 12-O-(2E,4E)-6-oxohexa-2,4-dienoylphorbol-13-acetate having a molecular formula $C_{28}H_{34}O_9$ of structural formula:

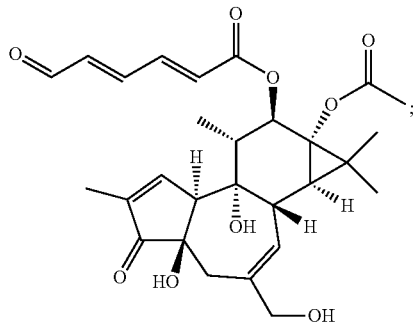

and

Formula IV: 12-O-(2E,4E)-6,7-dihydroxytetradeca-2,4-dienoylphorbol-13-acetate having a molecular formula $C_{36}H_{52}O_{10}$ of structural formula:

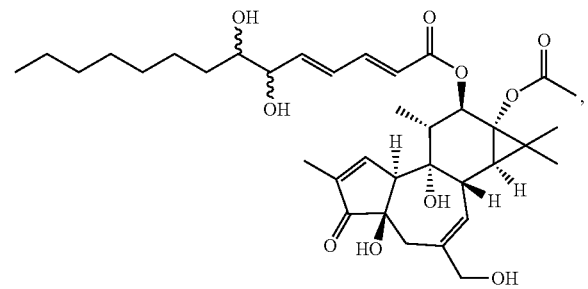

wherein Formula I derives from the subfraction AM4-4-9, Formula II derives from the subfractions AM4-3-6 and AM4-4-3, and Formulas III and IV derive from the subfraction AM4-3-13.

2. The method as claimed in claim 1, wherein phorbol ester of Formula I,

12-O-(2Z,4E,6E)-tetradeca-2,4,6-trienoylphorbol-13-acetate, was isolated from AM4-4-9.

Formula I

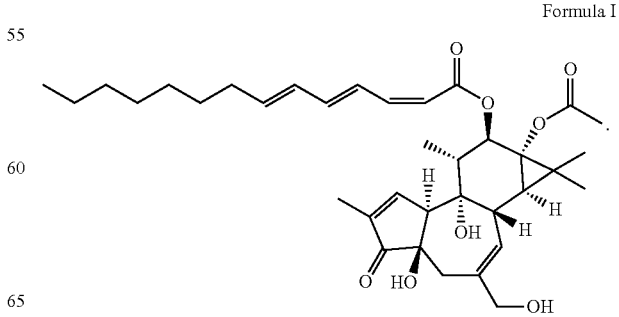

3. The method as claimed in claim 1, wherein phorbol ester of Formula II,
12-deoxy-13-O-acetoylphorbol-20-octadec-9-enoate, reported by now was isolated from AM4-3-6 and AM4-4-3

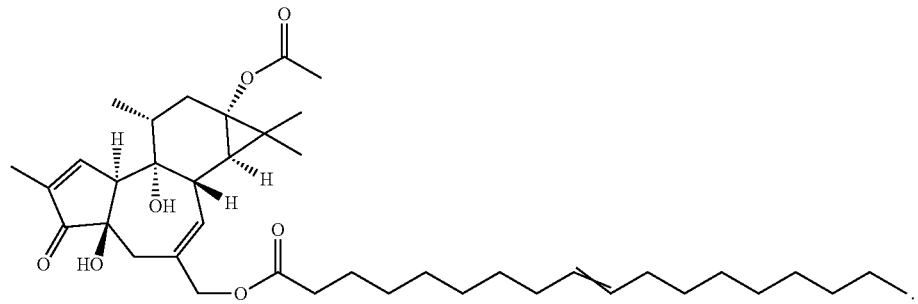

Formula II

4. The method as claimed in claim 1, wherein phorbol ester of Formula III,
12-O-(2E,4E)-6-oxohexa-2,4-dienoylphorbol-13-acetate, was isolated from AM4-3-13

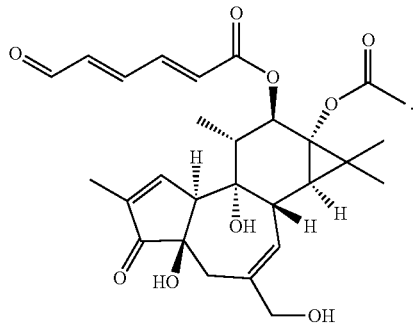

Formula III

5. The method as claimed in claim 1, wherein phorbol ester of Formula IV,
12-O-(2E,4E)-6,7-dihydroxytetradeca-2,4-dienoylphorbol-13-acetate, isolated from AM4-3-13

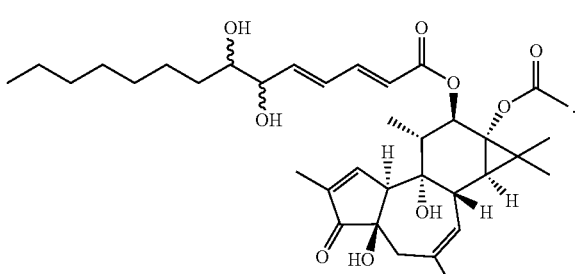

Formula IV

* * * * *